United States Patent
Albert

(10) Patent No.: US 9,579,062 B2
(45) Date of Patent: *Feb. 28, 2017

(54) METHODS AND SYSTEMS FOR ELECTRODE PLACEMENT

(71) Applicant: AliveCor, Inc., San Francisco, CA (US)

(72) Inventor: David E. Albert, San Francisco, CA (US)

(73) Assignee: ALIVECOR, INC., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/948,026

(22) Filed: Nov. 20, 2015

(65) Prior Publication Data

US 2016/0242697 A1 Aug. 25, 2016

Related U.S. Application Data

(63) Continuation of application No. 14/149,242, filed on Jan. 7, 2014, now Pat. No. 9,220,430.
(Continued)

(51) Int. Cl.
*A61B 5/044* (2006.01)
*A61B 5/00* (2006.01)
(Continued)

(52) U.S. Cl.
CPC ............ *A61B 5/684* (2013.01); *A61B 5/0402* (2013.01); *A61B 5/044* (2013.01); *A61B 5/0408* (2013.01); *A61B 5/70* (2013.01)

(58) Field of Classification Search
CPC .............. A61B 5/0402; A61B 5/04023; A61B 5/04025; A61B 5/044; A61B 5/061;
(Continued)

(56) References Cited

U.S. PATENT DOCUMENTS 3,717,857 A 2/1973 Evans
3,731,311 A 5/1973 Williams
(Continued)

FOREIGN PATENT DOCUMENTS

CH 675675 A5 10/1990
CN 101828915 A 9/2010
(Continued)

OTHER PUBLICATIONS

Adidas miCoach Pacer Review: Like Nike+, Only Better; printed from website http://gizmodo.com/5479456/adidas• printed on Mar. 4, 2010• 5 pages.
(Continued)

*Primary Examiner* — George Evanisko
(74) *Attorney, Agent, or Firm* — Wilson Sonsini Goodrich & Rosati

(57) ABSTRACT

Described herein are systems, devices and methods for guiding placement of electrodes, and particularly ECG electrodes on a patient. A picture of the patient's body the patient can be analyzed to determine where on the patient's body to place electrodes according to a predetermined, conventional or standard placement pattern. The methods, devices and systems may then guide a user in positioning or correcting the position of electrodes on the patient. For example, an image of the patient may be provided showing the correct position of the electrodes, which may act as a patient-specific map or guide. The electrode placement positions can correspond to conventional or standard 12-lead ECG electrode positions.

14 Claims, 13 Drawing Sheets

Related U.S. Application Data

(60) Provisional application No. 61/749,790, filed on Jan. 7, 2013.

(51) Int. Cl.
*A61B 5/0402* (2006.01)
*A61B 5/0408* (2006.01)

(58) Field of Classification Search
CPC .......... A61B 5/70; A61B 5/066; A61B 5/684; A61B 5/6841; A61B 5/6842
See application file for complete search history.

(56) References Cited

U.S. PATENT DOCUMENTS

| | | | |
|---|---|---|---|
| 3,768,014 A | 10/1973 | Smith et al. |
| 3,776,228 A | 12/1973 | Semler |
| 3,779,237 A | 12/1973 | Goeltz et al. |
| 3,779,249 A | 12/1973 | Semler |
| 3,782,367 A | 1/1974 | Hochberg et al. |
| 3,805,227 A | 4/1974 | Lester |
| 3,882,277 A | 5/1975 | DePedro et al. |
| 3,885,552 A | 5/1975 | Kennedy |
| 3,898,984 A | 8/1975 | Mandel et al. |
| 3,909,599 A | 9/1975 | Trott, Jr. et al. |
| 4,027,146 A | 5/1977 | Gilmore |
| 4,045,767 A | 8/1977 | Nishihara et al. |
| 4,083,366 A | 4/1978 | Gombrich et al. |
| 4,095,050 A | 6/1978 | Beachem et al. |
| 4,221,223 A | 9/1980 | Linden |
| 4,230,127 A | 10/1980 | Larson |
| 4,231,031 A | 10/1980 | Crowther et al. |
| 4,250,888 A | 2/1981 | Grosskopf |
| 4,281,664 A | 8/1981 | Duggan |
| 4,295,472 A | 10/1981 | Adams |
| 4,312,358 A | 1/1982 | Barney |
| 4,318,130 A | 3/1982 | Heuer |
| 4,364,397 A | 12/1982 | Citron et al. |
| 4,367,752 A | 1/1983 | Jimenez et al. |
| 4,409,984 A | 10/1983 | Dick |
| 4,531,527 A | 7/1985 | Reinhold, Jr. et al. |
| 4,567,883 A | 2/1986 | Langer et al. |
| 4,572,182 A | 2/1986 | Royse |
| 4,580,250 A | 4/1986 | Kago et al. |
| 4,583,553 A | 4/1986 | Shah et al. |
| 4,622,979 A | 11/1986 | Katchis et al. |
| 4,625,730 A | 12/1986 | Fountain et al. |
| 4,803,625 A | 2/1989 | Fu et al. |
| 4,889,131 A | 12/1989 | Salem et al. |
| 4,920,489 A | 4/1990 | Hubelbank et al. |
| 4,938,228 A | 7/1990 | Righter et al. |
| 4,938,229 A | 7/1990 | Bergelson et al. |
| 4,958,641 A | 9/1990 | Digby et al. |
| 4,981,141 A | 1/1991 | Segalowitz |
| 5,012,814 A | 5/1991 | Mills et al. |
| 5,023,906 A | 6/1991 | Novas |
| 5,025,794 A | 6/1991 | Albert et al. |
| 5,058,597 A | 10/1991 | Onoda et al. |
| 5,090,418 A | 2/1992 | Squires et al. |
| 5,111,396 A | 5/1992 | Mills et al. |
| 5,128,552 A | 7/1992 | Fang et al. |
| 5,136,555 A | 8/1992 | Gardos |
| 5,181,552 A | 1/1993 | Eiermann |
| 5,191,891 A | 3/1993 | Righter |
| 5,201,321 A | 4/1993 | Fulton |
| 5,218,969 A | 6/1993 | Bredesen et al. |
| 5,226,424 A | 7/1993 | Bible |
| 5,238,001 A | 8/1993 | Gallant et al. |
| D341,659 S | 11/1993 | Homayoun |
| 5,259,387 A | 11/1993 | DePinto |
| 5,301,679 A | 4/1994 | Taylor |
| 5,304,186 A | 4/1994 | Semler et al. |
| 5,313,953 A | 5/1994 | Yomtov et al. |
| 5,321,618 A | 6/1994 | Gessman |
| 5,333,616 A | 8/1994 | Mills et al. |
| 5,336,245 A | 8/1994 | Adams et al. |
| 5,337,752 A | 8/1994 | Reeves |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,360,005 A | 11/1994 | Wilk |
| 5,365,935 A | 11/1994 | Righter et al. |
| 5,410,587 A | 4/1995 | Grunwell |
| 5,417,222 A | 5/1995 | Dempsey et al. |
| 5,433,736 A | 7/1995 | Nilsson |
| 5,452,356 A | 9/1995 | Albert |
| 5,466,246 A | 11/1995 | Silvian |
| 5,467,773 A | 11/1995 | Bergelson et al. |
| 5,481,255 A | 1/1996 | Albert et al. |
| 5,503,158 A | 4/1996 | Coppock et al. |
| 5,518,001 A | 5/1996 | Snell |
| 5,522,396 A | 6/1996 | Langer et al. |
| 5,539,705 A | 7/1996 | Akerman et al. |
| D372,785 S | 8/1996 | Sabri |
| 5,544,661 A | 8/1996 | Davis et al. |
| 5,551,953 A | 9/1996 | Lattin et al. |
| 5,561,712 A | 10/1996 | Nishihara |
| 5,568,448 A | 10/1996 | Taniguchi et al. |
| 5,579,284 A | 11/1996 | May |
| D377,983 S | 2/1997 | Sabri |
| 5,608,723 A | 3/1997 | Felsenstein |
| 5,634,468 A | 6/1997 | Platt et al. |
| 5,652,570 A | 7/1997 | Lepkofker |
| 5,661,699 A | 8/1997 | Sutton |
| 5,675,325 A | 10/1997 | Taniguchi et al. |
| 5,678,562 A | 10/1997 | Sellers |
| 5,701,894 A | 12/1997 | Cherry et al. |
| 5,704,364 A | 1/1998 | Saltzstein et al. |
| 5,724,025 A | 3/1998 | Tavori |
| 5,730,143 A | 3/1998 | Schwarzberg |
| 5,735,285 A | 4/1998 | Albert et al. |
| 5,742,251 A | 4/1998 | Gerber |
| 5,748,103 A | 5/1998 | Flach et al. |
| 5,764,763 A | 6/1998 | Jensen et al. |
| 5,772,586 A | 6/1998 | Heinonen et al. |
| 5,818,788 A | 10/1998 | Kimura et al. |
| 5,825,718 A | 10/1998 | Ueki et al. |
| 5,827,179 A | 10/1998 | Lichter et al. |
| 5,840,020 A | 11/1998 | Heinonen et al. |
| 5,844,997 A | 12/1998 | Murphy, Jr. |
| 5,861,018 A | 1/1999 | Feierbach |
| 5,873,369 A | 2/1999 | Laniado et al. |
| 5,876,351 A | 3/1999 | Rohde |
| 5,877,675 A | 3/1999 | Rebstock et al. |
| 5,889,730 A | 3/1999 | May |
| 5,929,761 A | 7/1999 | Van der Laan et al. |
| D414,870 S | 10/1999 | Saltzstein |
| 5,970,388 A | 10/1999 | Will |
| 5,976,083 A | 11/1999 | Richardson et al. |
| 5,982,297 A | 11/1999 | Welle |
| 5,983,127 A | 11/1999 | DePinto |
| 6,008,703 A | 12/1999 | Perrott et al. |
| 6,024,705 A | 2/2000 | Schlager et al. |
| 6,037,704 A | 3/2000 | Welle |
| 6,048,319 A | 4/2000 | Hudgins et al. |
| D427,315 S | 6/2000 | Saltzstein |
| 6,072,396 A | 6/2000 | Gaukel |
| 6,083,248 A | 7/2000 | Thompson |
| 6,084,510 A | 7/2000 | Lemelson et al. |
| 6,102,856 A | 8/2000 | Groff et al. |
| 6,153,532 A | 11/2000 | Dow et al. |
| 6,159,147 A | 12/2000 | Lichter et al. |
| 6,198,394 B1 | 3/2001 | Jacobsen et al. |
| 6,224,548 B1 | 5/2001 | Gopinathan et al. |
| 6,236,889 B1 | 5/2001 | Soykan et al. |
| 6,264,614 B1 | 7/2001 | Albert et al. |
| 6,282,440 B1 | 8/2001 | Brodnick et al. |
| 6,282,441 B1 | 8/2001 | Raymond et al. |
| 6,289,238 B1 | 9/2001 | Besson et al. |
| 6,319,201 B1 | 11/2001 | Wilk |
| 6,343,049 B1 | 1/2002 | Toda |
| 6,363,139 B1 | 3/2002 | Zurek et al. |
| 6,364,834 B1 | 4/2002 | Reuss et al. |

(56) References Cited

U.S. PATENT DOCUMENTS

| | | |
|---|---|---|
| 6,366,871 B1 | 4/2002 | Geva |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |
| 6,478,736 B1 | 11/2002 | Mault |
| 6,507,734 B1 | 1/2003 | Berger et al. |
| 6,513,532 B2 | 2/2003 | Mault et al. |
| 6,549,756 B1 | 4/2003 | Engstrom |
| 6,558,320 B1 | 5/2003 | Causey, III et al. |
| 6,579,231 B1 | 6/2003 | Phipps |
| 6,595,929 B2 | 7/2003 | Stivoric et al. |
| 6,600,471 B2 | 7/2003 | Lee et al. |
| 6,605,038 B1 | 8/2003 | Teller et al. |
| 6,612,985 B2 | 9/2003 | Eiffert et al. |
| 6,616,613 B1 | 9/2003 | Goodman |
| 6,636,761 B2 | 10/2003 | Brodnick |
| 6,717,983 B1 | 4/2004 | Toda |
| 6,790,178 B1 | 9/2004 | Mault et al. |
| 6,804,558 B2 | 10/2004 | Haller et al. |
| 6,820,057 B1 | 11/2004 | Loch et al. |
| 6,845,263 B2 | 1/2005 | Kawaguchi |
| 6,893,396 B2 | 5/2005 | Schulze et al. |
| 6,928,535 B2 | 8/2005 | Yamashita et al. |
| 6,950,681 B2 | 9/2005 | Hofmann |
| 6,970,737 B1 | 11/2005 | Brodnick et al. |
| 6,987,965 B2 | 1/2006 | Ng et al. |
| 7,018,339 B2 | 3/2006 | Birnbaum et al. |
| 7,020,508 B2 | 3/2006 | Stivoric et al. |
| 7,031,745 B2 | 4/2006 | Shen |
| 7,061,381 B2 | 6/2006 | Forcier et al. |
| 7,103,407 B2 | 9/2006 | Hjelt et al. |
| 7,107,095 B2 | 9/2006 | Manolas |
| 7,108,659 B2 | 9/2006 | Ross et al. |
| 7,153,262 B2 | 12/2006 | Stivoric et al. |
| 7,162,294 B2 | 1/2007 | Rowlandson et al. |
| 7,188,151 B2 | 3/2007 | Kumar et al. |
| 7,222,054 B2 | 5/2007 | Geva |
| 7,236,818 B2 | 6/2007 | McLeod et al. |
| 7,257,448 B2 | 8/2007 | Crowe et al. |
| 7,260,429 B2 | 8/2007 | Siejko et al. |
| 7,261,690 B2 | 8/2007 | Teller et al. |
| 7,285,090 B2 | 10/2007 | Stivoric et al. |
| 7,319,425 B2 | 1/2008 | Fiorenza et al. |
| 7,324,836 B2 | 1/2008 | Steenstra et al. |
| 7,349,574 B1 | 3/2008 | Sodini et al. |
| 7,351,207 B2 | 4/2008 | Priemer |
| 7,354,400 B2 | 4/2008 | Asafusa et al. |
| 7,383,297 B1 | 6/2008 | Atsmon et al. |
| 7,415,304 B2 | 8/2008 | Rowlandson et al. |
| 7,444,116 B2 | 10/2008 | Ivanov et al. |
| 7,509,159 B2 | 3/2009 | Xue et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,596,405 B2 | 9/2009 | Kurzweil et al. |
| 7,603,148 B2 | 10/2009 | Michalak |
| 7,654,148 B2 | 2/2010 | Tomlinson, Jr. et al. |
| 7,657,479 B2 | 2/2010 | Henley |
| 7,668,589 B2 | 2/2010 | Bauer |
| 7,689,437 B1 | 3/2010 | Teller et al. |
| 7,701,895 B2 | 4/2010 | Gehasie et al. |
| 7,733,224 B2 | 6/2010 | Tran |
| 7,742,808 B2 | 6/2010 | Nissila et al. |
| 7,819,814 B2 | 10/2010 | Gavriely et al. |
| 7,846,104 B2 | 12/2010 | MacQuarrie et al. |
| 7,904,160 B2 | 3/2011 | Brodnick et al. |
| 7,945,064 B2 | 5/2011 | O'Brien et al. |
| 7,946,959 B2 | 5/2011 | Shum et al. |
| 7,955,273 B2 | 6/2011 | Rahe-Meyer |
| 7,983,749 B2 | 7/2011 | Warren |
| 8,019,609 B2 | 9/2011 | Tamir et al. |
| 8,034,006 B2 | 10/2011 | Celik-Butler et al. |
| 8,062,090 B2 | 11/2011 | Atsmon et al. |
| 8,078,136 B2 | 12/2011 | Atsmon et al. |
| 8,078,278 B2 | 12/2011 | Penner |
| 8,126,566 B2 | 2/2012 | Stahmann et al. |
| 8,126,728 B2 | 2/2012 | Dicks et al. |
| 8,130,093 B2 | 3/2012 | Mazar et al. |
| 8,150,750 B2 | 4/2012 | Ray |
| 8,160,276 B2 | 4/2012 | Liao et al. |
| 8,165,677 B2 | 4/2012 | Von Arx et al. |
| 8,224,429 B2 | 7/2012 | Prstojevich et al. |
| 8,265,907 B2 | 9/2012 | Nanikashvili et al. |
| 8,275,635 B2 | 9/2012 | Stivoric et al. |
| 8,282,550 B2 | 10/2012 | Rasdal et al. |
| 8,285,356 B2 | 10/2012 | Bly et al. |
| 8,301,232 B2 | 10/2012 | Albert et al. |
| 8,301,236 B2 | 10/2012 | Baumann et al. |
| 8,323,188 B2 | 12/2012 | Tran |
| 8,328,718 B2 | 12/2012 | Tran |
| 8,332,233 B2 | 12/2012 | Ott et al. |
| 8,364,250 B2 | 1/2013 | Moon et al. |
| 8,369,936 B2 | 2/2013 | Farringdon et al. |
| 8,374,688 B2 | 2/2013 | Libbus et al. |
| 8,449,471 B2 | 5/2013 | Tran |
| 8,500,636 B2 | 8/2013 | Tran |
| 8,509,882 B2 | 8/2013 | Albert et al. |
| 8,519,835 B2 | 8/2013 | Dunko |
| 8,543,185 B2 | 9/2013 | Yuen et al. |
| 8,548,770 B2 | 10/2013 | Yuen et al. |
| 9,220,430 B2 * | 12/2015 | Albert .................. A61B 5/70 |
| 2001/0027384 A1 | 10/2001 | Schulze et al. |
| 2001/0031998 A1 | 10/2001 | Nelson et al. |
| 2001/0051766 A1 | 12/2001 | Gazdzinski |
| 2002/0016541 A1 | 2/2002 | Glossop |
| 2002/0032386 A1 | 3/2002 | Sackner et al. |
| 2002/0111556 A1 | 8/2002 | Wegner |
| 2002/0143576 A1 | 10/2002 | Nolvak et al. |
| 2003/0004425 A1 | 1/2003 | Narimatsu et al. |
| 2003/0093002 A1 | 5/2003 | Kuo |
| 2003/0107487 A1 | 6/2003 | Korman et al. |
| 2003/0117987 A1 | 6/2003 | Brebner |
| 2003/0149344 A1 | 8/2003 | Nizan |
| 2003/0193839 A1 | 10/2003 | Singh |
| 2004/0034284 A1 | 2/2004 | Aversano et al. |
| 2004/0044292 A1 | 3/2004 | Yasushi et al. |
| 2004/0059205 A1 | 3/2004 | Carlson et al. |
| 2004/0117212 A1 | 6/2004 | Kong et al. |
| 2004/0143403 A1 | 7/2004 | Brandon et al. |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0225199 A1 | 11/2004 | Evanyk et al. |
| 2004/0236819 A1 | 11/2004 | Anati et al. |
| 2004/0266407 A1 | 12/2004 | Lee et al. |
| 2004/0266480 A1 | 12/2004 | Hjelt et al. |
| 2005/0014531 A1 | 1/2005 | Findikli |
| 2005/0027207 A1 | 2/2005 | Westbrook et al. |
| 2005/0078533 A1 | 4/2005 | Vyshedskiy et al. |
| 2005/0124864 A1 | 6/2005 | Mack et al. |
| 2005/0234353 A1 | 10/2005 | Xue et al. |
| 2006/0022833 A1 | 2/2006 | Ferguson et al. |
| 2006/0047215 A1 | 3/2006 | Newman et al. |
| 2006/0173259 A1 | 8/2006 | Flaherty et al. |
| 2006/0190045 A1 | 8/2006 | Marcus et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0032731 A1 | 2/2007 | Lovejoy et al. |
| 2007/0063850 A1 | 3/2007 | Devaul et al. |
| 2007/0106179 A1 | 5/2007 | Bagha et al. |
| 2007/0156060 A1 | 7/2007 | Cervantes |
| 2007/0254604 A1 | 11/2007 | Kim |
| 2007/0265038 A1 | 11/2007 | Kim |
| 2008/0009759 A1 | 1/2008 | Chetham |
| 2008/0058670 A1 | 3/2008 | Mainini |
| 2008/0112885 A1 | 5/2008 | Okunev et al. |
| 2008/0146890 A1 | 6/2008 | LeBoeuf et al. |
| 2008/0171945 A1 | 7/2008 | Dotter |
| 2008/0177162 A1 | 7/2008 | Bae et al. |
| 2008/0198872 A1 | 8/2008 | Pierce |
| 2008/0214903 A1 | 9/2008 | Orbach |

(56) References Cited

U.S. PATENT DOCUMENTS

| | | |
|---|---|---|
| 2008/0228045 A1 | 9/2008 | Gao et al. |
| 2008/0293453 A1 | 11/2008 | Atlas et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0273467 A1 | 11/2009 | Elixmann et al. |
| 2009/0279389 A1 | 11/2009 | Irie |
| 2009/0287067 A1 | 11/2009 | Dorogusker et al. |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0035927 A1 | 2/2010 | Ojika et al. |
| 2010/0042008 A1 | 2/2010 | Amitai et al. |
| 2010/0049006 A1 | 2/2010 | Magar et al. |
| 2010/0049037 A1 | 2/2010 | Pinter et al. |
| 2010/0063381 A1 | 3/2010 | Greiser |
| 2010/0069735 A1 | 3/2010 | Berkner |
| 2010/0076276 A1 | 3/2010 | Gilland |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0184479 A1 | 7/2010 | Griffin, Jr. |
| 2010/0204758 A1 | 8/2010 | Boon et al. |
| 2010/0208434 A1 | 8/2010 | Kim et al. |
| 2010/0217099 A1 | 8/2010 | Leboeuf et al. |
| 2010/0217100 A1 | 8/2010 | Leboeuf et al. |
| 2010/0217345 A1 | 8/2010 | Wolfe et al. |
| 2010/0256509 A1 | 10/2010 | Kuo et al. |
| 2010/0281261 A1 | 11/2010 | Razzell |
| 2010/0298711 A1 | 11/2010 | Pedersen et al. |
| 2010/0324378 A1 | 12/2010 | Tran et al. |
| 2010/0331631 A1 | 12/2010 | Maclaughlin |
| 2011/0015496 A1 | 1/2011 | Sherman et al. |
| 2011/0035927 A1 | 2/2011 | Griffin et al. |
| 2011/0066042 A1 | 3/2011 | Pandia et al. |
| 2011/0117529 A1 | 5/2011 | Barash et al. |
| 2011/0134725 A1 | 6/2011 | Su et al. |
| 2011/0160601 A1 | 6/2011 | Wang et al. |
| 2011/0235466 A1 | 9/2011 | Booij et al. |
| 2011/0301439 A1 | 12/2011 | Albert et al. |
| 2012/0051187 A1 | 3/2012 | Paulson |
| 2012/0053424 A1 | 3/2012 | Kenalty et al. |
| 2012/0071734 A1 | 3/2012 | Shimuta et al. |
| 2012/0123891 A1 | 5/2012 | Patel |
| 2012/0127833 A1 | 5/2012 | Ghen et al. |
| 2012/0143018 A1 | 6/2012 | Skidmore et al. |
| 2012/0147921 A1 | 6/2012 | Conti et al. |
| 2012/0157019 A1 | 6/2012 | Li |
| 2012/0158090 A1 | 6/2012 | Chavan et al. |
| 2012/0171963 A1 | 7/2012 | Tsfaty |
| 2012/0179056 A1 | 7/2012 | Moulder et al. |
| 2012/0316413 A1 | 12/2012 | Liu et al. |
| 2013/0030259 A1 | 1/2013 | Thomsen et al. |
| 2013/0085364 A1 | 4/2013 | Lu et al. |
| 2013/0197320 A1 | 8/2013 | Albert et al. |
| 2013/0236980 A1 | 9/2013 | Moretti et al. |
| 2013/0261414 A1 | 10/2013 | Tal et al. |
| 2013/0331663 A1 | 12/2013 | Albert et al. |
| 2014/0194760 A1 | 7/2014 | Albert |

FOREIGN PATENT DOCUMENTS

| | | |
|---|---|---|
| CN | 201918016 U | 8/2011 |
| CN | 102347804 A | 2/2012 |
| DE | 2506936 A1 | 9/1976 |
| DE | 4212670 A1 | 1/1994 |
| EP | 0631226 A1 | 12/1994 |
| EP | 1782229 A2 | 5/2007 |
| EP | 1181888 B1 | 9/2007 |
| EP | 1238633 B1 | 10/2008 |
| EP | 2030565 A1 | 3/2009 |
| EP | 2116183 B1 | 2/2012 |
| FR | 2740426 A1 | 4/1997 |
| GB | 2181554 A | 4/1987 |
| GB | 2408105 A | 5/2005 |
| JP | S59122032 A | 7/1984 |
| JP | S59190742 A | 10/1984 |
| JP | S63072231 A | 4/1988 |
| JP | S63294044 A | 11/1988 |
| JP | H01244328 A | 9/1989 |
| JP | H05167540 A | 7/1993 |
| JP | H06326669 A | 11/1994 |
| JP | 2002191562 A | 7/2002 |
| JP | 2002261731 A | 9/2002 |
| JP | 2003010177 A | 1/2003 |
| JP | 2005295378 A | 10/2005 |
| JP | 2012065073 A | 3/2012 |
| MX | 2009011781 A | 5/2011 |
| WO | WO-8200910 A1 | 3/1982 |
| WO | WO-8805282 A1 | 7/1988 |
| WO | WO-9008361 A1 | 7/1990 |
| WO | WO-9206551 A1 | 4/1992 |
| WO | WO-9731437 A1 | 8/1997 |
| WO | WO-9838611 A1 | 9/1998 |
| WO | WO-9944494 A1 | 9/1999 |
| WO | WO-0041620 A1 | 7/2000 |
| WO | WO-0147597 A2 | 7/2001 |
| WO | WO-0157619 A2 | 8/2001 |
| WO | WO-02080762 A1 | 10/2002 |
| WO | WO-03075118 A2 | 9/2003 |
| WO | WO-03094720 A1 | 11/2003 |
| WO | WO-2004037080 A1 | 5/2004 |
| WO | WO-2006001005 A2 | 1/2006 |
| WO | WO-2007014545 A2 | 2/2007 |
| WO | WO-2007088315 A1 | 8/2007 |
| WO | WO-2008005015 A1 | 1/2008 |
| WO | WO-2008066682 A2 | 6/2008 |
| WO | WO-2010025166 A1 | 3/2010 |
| WO | WO-2010108287 A1 | 9/2010 |
| WO | WO-2010113354 A1 | 10/2010 |
| WO | WO-2010144626 A1 | 12/2010 |
| WO | WO-2011006356 A1 | 1/2011 |
| WO | WO-2011008838 A1 | 1/2011 |
| WO | WO-2011014292 A1 | 2/2011 |
| WO | WO-2011022942 A1 | 3/2011 |
| WO | WO-2011040877 A1 | 4/2011 |
| WO | WO-2011040878 A1 | 4/2011 |
| WO | WO-2011113070 A1 | 9/2011 |
| WO | WO-2011137375 A2 | 11/2011 |
| WO | WO-2012046158 A1 | 4/2012 |
| WO | WO-2012108895 A1 | 8/2012 |
| WO | WO-2012129413 A1 | 9/2012 |
| WO | WO-2012160550 A1 | 11/2012 |
| WO | WO-2013036307 A1 | 3/2013 |
| WO | WO-2013066642 A1 | 5/2013 |
| WO | WO-2013093690 A1 | 6/2013 |
| WO | WO-2013122788 A1 | 8/2013 |
| WO | WO-2013138500 A1 | 9/2013 |
| WO | WO-2013155196 A2 | 10/2013 |
| WO | WO-2013192166 A1 | 12/2013 |

OTHER PUBLICATIONS

Australian Design Awards. Heartplus Micro; printed from website http://www.designawards.com/au; printed on Apr. 12, 2002 • 6 pages.

Bajaj, M.D.; "Event Recording in Ambulatory Patients with Syncopal Events"; University of Kansas; Wichita, Kansas; (no date); pp. 15-18; printed on or before Apr. 14, 2010.

Bluetooth. Headset Profile (HSP), printed from website http://bluetooth.com/English/Technology/Works/Pates/HSP.asgx, printed on May 12, 2010.

Bramanti et al., Multichannel telemetric system for biomedical signals via switched telephone lines, Medical and Biological Engineering and Computing, Sep. 1982, vol. 20, No. 5, pp. 653-656.

(56) References Cited

OTHER PUBLICATIONS

Burke, "A Micropower Dry-Electrode ECG Preamplifier", IEEE Transactions on Biomedical Engineering, Feb. 2000, vol. 47, No. 2, pp. 155-162.

Card Guard CG-6108 ACT Ambulatory Cardiac Telemetry Brochure; Card Guard; The Telemedicine Company: Switzerland; 2006; 2 pages.

Cardiocomm Solutions; GEMS AIR. (PC based ECG management) printed from website http://www.cardiocommsolutions/com; printed on Mar. 19, 2010; 1 page.

Charuvastra. Transtelephonic Cardiac Event Recording for Arrhythmia Surveillance; printed from website http://tchin.org/resource room/c art• printed on Mar. 26, 2010• 2 pages.

Cheng, Allen C.; "Real-Time Cardiovascular Diseases Detection on a Smartphone"; Departments of Electrical and Computer Engineering, Bioengineering, Neurological Surgery and Computer Science; University of Pittsburgh; Pittsburgh, PA; printed on or before Apr. 14, 2010.

Creative. PC-80B Portable ECG Monitor w/sd card extension slot; printed from website www.amazon.com/Portable-Monitor-extension-leather-shipping/dp/B0010jWKUE; printed on Feb. 4, 2010• 5 pages.

Deveau, "Health Care eyes smart phones to heal ills", printed from the website http://www.theQiobeandmail.com on Sep. 17, 2009, 4 pages.

Dinh. Heart activity monitoring on smartphone. IPCBEE-Int conf Biomedical Eng and Technol. Jun. 17-19, 2011. 11:45-49.

Dobrev, et al., Bootstrapped two-electrode biosignal amplifier, Med Bioi Eng Comput, 2008, 7 pages.

Dolan; Qualcomm launches ECG smartphone program in China; Sep. 8, 2011; 11 pgs.; retrieved Mar. 19, 2014 from the internet (http://mobihealthnews.com/13092/qualcomm-launches-ecg-smartphone-program-in-china/).

Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http:I/hypertextbook.com/facts/2003/ChrisDAmbrose.shtml).

Favorite Plus. Handheld Easy ECG Monitor—Handheld Easy EKG Monitor; printed from website www.favoriteplus.com/easy-ecg-handgeld-monitor-fp; printed on Feb. 4, 2010; 2 pages.

Favorite Plus. Handheld ECG Monitor—Handheld EKG Monitor at Favoriteplus.com; printed from website www.favoriteplus.com/handheld-ecg-ekg-monitor; printed on Feb. 4, 2010; 3 pages.

Favorite Plus. Handheld ECG Monitor—Handheld EKG Monitor InstantCheck; printed from website http://www.favoriteplus.com/instanchcheck-hand held-ecg-ekg-monitor; printed on Feb. 4, 2010; 2 pages.

Ferrick, M.D.; "Holter Monitoring and cardiac Event Recording in Assessing Symptomatic Patients"; Albert Einstein College of Medicine; Bronx, New York; (no date)• pp. 11-14• printed on or before Apr. 14, 2010.

Fulford-Jones, et al., "A Portable, Low-Power, Wireless Two-Lead EKG System", Division of Engineering and Applied Sciences, Harvard University, Sep. 2004, 4 pages.

Garabelli et al. Accuracy and Novelty of an Inexpensive iPhone-based Event Recorder (Presentation Poster/Abstract) Heart Rhythm 2012, 33rd Annual Scientific Session. SP23. Innovation Poster Session II. No. IA02-1; May 11, 2012.

GBI Portal. Qualcomm's wireless reach mHealth project to improve cardiovascular disease in resource scarce China; Feb. 17, 2012; 7 pgs. Retrieved Mar. 19, 2014 from www.intergrallc.com/2012/02/17/qualcooms-wireless-reach-mhealth-project-to-improve-cardiovascular-disease-in-resource-scarce-china/.

Gillette, M.D.; "Diagnosis of Pediatric Arrhythmias with Event Recording"; Medical University of South Carolina; Charleston, South Carolina; (no date); pp. 25-32; printed on or before Apr. 14, 2010.

Grier, James W.; "How to use 1-lead ECG recorders to obtain 12-lead resting ECGs and exercise ("stress") ECGs"; Department of Biological Sciences: printed from website http://www.ndsu.edu/pubweb/rvgrier; printed on Jun. 7, 21010; 13 pages.

Hannaford, Kat; "How to Turn Your iPhone Into a Laser, Fan or Flashlight"; printed from website htto://m.qizmodo.com/5534904• printed on Feb. 3, 2011.

Hayes, M.D.; "Approaches to Diagnosing Transient Arhythmias" An Overview; Mayo Clinic; Rochester Minnesota; (no date); pp. 7-10; printed on or before Apr. 14, 2010.

Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.orglhlasurvival1.html).

Hickey, et al. Detection of Recurrent Atrial Fibrillation Utilizing Novel Technology. Journal of Atrial Fibrillation. Dec. 2013-Jan. 2014; 6(4):50-52.

Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/October2007/Ciinca1HuangOctober2007.aspx).

IMEC News; IMEC extends flexible ECG patch to enable arrhythmia detection; printed from website http://www2.imec.be/imeC' printed on Aug. 18, 2009 1 page.

Instromedix. Cardiac Event Recording FAQ's; Instromedix A Card Guard Company, San Diego, CA.; printed from website www.instromedix.com/pdf/products/cardiac; printed on or before Apr. 14, 2010.

Instromedix. The Arrhythmia Monitoring System; King of Hearts Express AF Recorder Brochure from Instromedix• A CardGuard Company; Rosemont IL; 2004• 3 pages.

Jenkins II, W.; Time/Frequency Relationships for an FFT-Based Acoustic Modem; Naval Postgraduate School; pp. 1-1 02; Sep. 2010 (http://edocs.nps.edu/npspubs/scholarly/theses/201 0/Sep/1 OSep__Jenkins.pdf) printed Oct. 2, 2013.

Kim, et al., "Detection of Atrial Fibrillation Episodes using Multiple Heart Rate Variabili!Y_Features in Different Time Periods", 2008, 4 pages.

Koerner. The Author's Metrics; Wired Magazine Article; New York, NY; Jul. 2009; p. 93-126.

Kumparak, Greg; "Visa officially announces their case that turns your iPhone into a credit card (and we've got pies!)"; May 17, 2010; printed from website www.mobilecrunch.com• printed on Feb. 3, 2011.

Lau, et al. iPhone ECG application for community screening to detect silent atrial fibrillation: A novel technology to prevent stroke. Int J Cardiol. Apr. 30, 2013;165(1):193-4.

Lau, et al. Performance of an Automated iPhone ECG Algorithm to Diagnose Atrial Fibrillation in a Community AF Screening Program (SEARCH-AF). Heart, Lung and Circulation. 2013; 22:S205.

Lau et al. Validation of an iPhone ECG application suitable for community screening for silent atrial fibrillation—A novel way to prevent stroke (Presentation Abstract 16810); American Heart Association 2012 Scientific Sessions and Resuscitation Science Symposium; 126(1); Nov. 20, 2012.

Leijdekkers et al., "Trial Results of a Novel Cardiac Rhythm Management System using Smart Phones and wireless ECG Sensors", Proceedings of the th International Conf. on Smart homes and health Telematics., Jul. 1-3, 2009, Tours, France.

Levkov et al., "Removal of power-line interference from the ECG: a review of the subtraction procedure" BioMedical Engineering Online 2005, printed from website httg://www.biomedical-engineeringonline.com/contenU4/1/50 pp. 1-18.

Lowres, et al. Screening Education and Recognition in Community pHarmacies of Atrial Fibrillation to prevent stroke in an ambulant population aged >=65 years (SEARCH-AF stroke prevention study): a cross-sectional study protocol. BMJ Open. Jun. 25, 2012; 2(3); pii: e001355. doi: 10.1136/bmjopen-2012-001355.

M Med Choice. Handheld ECG Monitor Brochure; M Med Choice, Beijing Choice Electronic Technology Co. LTD.• published on or before Apr. 14, 2010.

M Med Choice. Handheld ECG Monitor MD100A1; printed from website http://www.choicemmed.com/productshow.as_p; printed on Dec. 28, 2009; 2 pages.

(56) References Cited

OTHER PUBLICATIONS

M Med Choice. Handheld ECG Monitor MD100B; printed from website http://www.choicemmed.com/productshow.asp; printed on Dec. 28, 2009. 2 pages.
M Med Choice printed from website http://www.choicemmed.con/1xwm .asp; printed on Dec. 28, 2009• 1 page.
MacFarlane, et al. Resting 12-lead ECG electrode placement and associated problems; SCST update 1995; 15pgs. Printed Feb. 18, 2014 from www.scst.org.uk/resources/RESTING_12.pdf.
Mauvila ECG Tutorial; Basic ECG Interpretation Tutorial; Sections 1-12; printed from website http://mauvila.com/ECG/ecg.htm• printed on Mar. 26, 2010• 56 pages.
Medgadget. Zio Patch Wins Medical Design Award MedGadget internet journal of emerging medical technologies, printed from website http://medaadaet.com/archives/2010/04/zio_patch_wins_medial_design_award_1.html.
MiCardioMobile: Remote Wireless Cardiac Rehabilitation Monitoring printed from website htto://alivetec.cable.nu/cardiomobile• printed on or before Apr. 14, 2010.
Mobility Mind. Use your Treo 650 as a portable ECG monitoring device, Mobility Mind Celebrating mobile Internet lifestyle and culture, Sep. 14, 2005, printed from website httg://www.treotoday.net/2005/09/14/use-your-treo-650-as-a-portab le-ecg-monitoring-device/.
Modem Protocols Explained; ftp://kermit.columbia.edu/kermit/cu/protocol.html; 5 pgs.; printed Oct. 2, 2013.
Modem Tutorial; http://www.Isu.edu/OCS/its/unix/tutoriai/ModemTutoriai/ModemTutorial.html; 2 pgs.; printed Oct. 2, 2013.
Muench, Frederick, PhD; "HRV: The Manurfacturers and Vendors Speak; The portable StressEraser Heart Rate Variability Biofeedback Device: Background and Research"• Biofeedback vol. 36 Issue 1, pp. 35-39• published Spring 2008.
Murph. RedEye mini converts iPhone, iPad or iPod touch into IR-beaming universal remote; printed from website http://www.engadget.com/2010/03/02/redeye; printed on Mar. 2, 2010; 3 pages.
Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).
Neuroreille; Audiometry; web version as of Oct. 14, 2008; 1 pg.; printed Jun. 6, 2012 (http://www.neuroreille.com/promenade/english/audiometry/audiometry.htm).
Omron Portable ECG EKG Handheld HCG-801 Monitor; printed from website http://www.amazon.com/Omron-Portable-Handheld-HCG-801-Monitor/dp/B0019WH3EO• printed on Feb. 24, 2010. 5 pages.
Omron Portable ECG Monitor; printed from website http://www.target.com/gp/detail.html; printed on Mar. 26, 2010• 1 page.
Oresko, et al., "Detecting Cardiovascular Diseases via Real-Time Electrocardiogram Processing on a Smartphone", 2009 Workshop on Biomedicine in Computing: Systems, Architectures, and Circuits, pp. 13-16.
Perez, Sarah; No NFC? No Problem; New Startup Zoosh Provides Workaround Technology (Jun. 20, 2011); printed on or before Jun. 27, 2011 from website; 2 pgs.; (http://www.readwriteweb.com/archives).
Prystowsky, M.D.; "Chairmans Introduction"; Duke University Medical Center; Indianapolis, Indiana• (no date)• pp. 5-6• printed on or before Apr. 14, 2010.
Prystowsky, M.D.; "Chairmans Summary"; Duke University Medical Center; Indianapolis Indiana; (no date); pp. 39-40• printed on or before Apr. 14, 2010.
Prystowsky, M.D., "The Clinical Application, Diagnostic Yield and Cost Considerations of Cardiac Event Recorders", Indianapolis, Indiana (no date) pp. 19-23. printed on or before Apr. 14, 2010.
Puurtinen, et al., Best Electrode Locations for a Small Bipolar ECG Device: Signal Strength Analysis of Clinical Data, Annals of Biomedical Engineering, vol. 37, No.s 2, Feb. 2009 (© 2008) pp. 331-336.
Raju Heart-Rate and EKG Monitor Using the MSP430FG439, SLAA280-Oct. 2005-Revised Sep. 2007, 11 pages.
Read-My-Heart. ECG Machine Handheld Read MyHeart; (product item No. HH-3413) printed from website http://www.helioliving.com/ECG-Machi ne-Handheld-ReadMyHea rt; printed on Feb. 4, 2010; 1 page.
Readmyheart Personal Handheld ECG Monitor with Free Illustrator Book & Free Electrodes V2.2; printed from website http://www.amazon.com/Readmyheart-Personai-Handheld-illustrator-Eiectrodes/dp/B0010AN63W; printed on Mar. 26, 2010; 4 pages.
Ricker. Square payment dongle demoed for iPhone toting hippies and you (video); printed from website http://www.engadget.com/2010/01/18/square-payment; printed on Jan. 18, 2010; 6 pages.
Rockwood. The Networked Body Magazine Article from Fast Talk Magazine; Jul./Aug. 2009; pp. 19-26.
Salahuddin, et al., "Ultra Short Term Analysis of Heart Rate Variability using Normal Sinus Rhythm and Atrial Fibrillation ECG Data", Engineering in Medicine and Biology Society, Aug. 2007, pp. 4656-4659.
Saxon, et al. iPhone rhythm strip—the implications of wireless and ubiquitous heart rate monitoring. JACC; 59(13): E726; Mar. 2012.
Saxon. Ubiquitous Wireless ECG Recording: A Powerful Tool Physicians Should Embrace. J Cardiovasc Electrophysiol. 24(4): pp. 480-483; Apr. 2013.
Semler, M.D.; "The Future of Cardiac Event Monitoring"; St. Vincent Hospital and Medical Center; Portland Oregon; (no date); pp. 33-37; printed on or before Apr. 14, 2010.
SFO Medical. Choice Portable Handheld ECG EKG Monitor; printed from website http://www.amazon.com/Choice-Portable-Handheld-ECG-Monitor/dp/B001Q74VOM; printed on Mar. 26, 2010; 1 page.
Shenzhen New Element Med. Equipment. Wireless ECG Monitoring System, printed from website http://www.alibaba.com/product-gs/248168581/Wireless_ECG_Monitoring_system.html., printed on Mar. 26, 2010.
Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.
Smith. Smartphone may keep the cardiologist away, The Independent, Health & Families, Mar. 5, 2010, printed from website http://www.independent.co.uk/life-style/health-and-families/healthnews/smartghone-may-keep-the-cardiologist-away-1916652.html, printed on Mar. 26, 2010.
Stevens, "Apple's Seamlessly Embedded Heart Rate Monitor could turn the iPhone into a new-age mood ring", printed from the website http://www.enaadaet.com on May 6, 2010, 3 pages.
Taleb Medical. Observer Hand-held ECG Monitor MD100B; (no date); printed on or before Apr. 14, 2010.
Tei, et al., New index of combined systolic and diastolic myocardial performance: a simple and reproducible measure of cardiac function—a study in normals and dilated cardiomyopathy; J Cardiol.; 26(6):357-366; Dec. 1995.
Texas Instruments. Information for Medical Applications, "Biophysical Monitoring-Electrocardiogram (ECG) Front End", Apr. 2004, 2 pages.
Tschida. Power A's New Case Turns Your iPhone Into a Universal Remote; printed from website http://appadvice.com/appnn; printed on Mar. 1, 2010• 2 pages.
U.S. Appl. No. 13/969,446, filed Aug. 16, 2013.
U.S. Appl. No. 14/015,303, filed Aug. 30, 2013.
U.S. Appl. No. 14/076,076, filed Nov. 8, 2013.
U.S. Appl. No. 14/217,032, filed Mar. 17, 2014.
U.S. Appl. No. 14/252,044, filed Apr. 14, 2014.
Vanhemert, Kyle; "XWave Headset Lets You Control iPhone Apps With Your Brain"; Sep. 8, 2010; printed from website http://gizmodo.com; printed on Sep. 8, 2010.

(56) References Cited

OTHER PUBLICATIONS

Vitaphone. Telemedicine since 1999: Modern health management is our special subject. 3 pgs. Retrieved Mar. 19, 2014 from www.vitaphone.de/en/company/history-of-vitaphone/.

Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).

Wikipedia; Aliasing; web version as of Apr. 3, 2011; S pgs.; printed Jun. 6, 2012 (http://liveweb.archive.org/http://en.wikipedia.org/w/index.php?title=Aiiasing&oldid=422141882).

Wikipedia; Hearing Range; web version as of Feb. 6, 2010; S pgs.; printed Jun. 6, 2012 (http://web.archive.org/web/201 00206213741/http://en.wikipedia.org/wiki/Hearing_range).

Wikipedia ."Pulse oximetry", printed from website httg://en.wikigedia.orq on May 10, 2010, 4 pages.

Wisneski, C.; Ultrasonic Local Area Communication; http://alumni.media.mit.edu/-wiz/ultracom.html; 2 pgs.; printed Oct. 2, 2013.

Woodward et al; "Bio-Potentiai-To-Frequency Converter/Modulator"; Electronic Design• Aug. 1999• p. 117.

Ziegler, Chris; "EPI Life phone sports ECG function, can let doctors know if you're gonna make it"; printed from website www.enoadoet.com/2010/06/; Jun. 17, 2010.

\* cited by examiner

METHODS AND SYSTEMS FOR ELECTRODE PLACEMENT

CROSS REFERENCE TO RELATED APPLICATIONS

This application is a continuation of U.S. patent application Ser. No. 14/149,242 filed Jan. 7, 2014 which claims priority to U.S. Provisional Patent Application No. 61/749,790, titled "METHODS AND SYSTEMS FOR ELECTRODE PLACEMENT," filed on Jan. 7, 2013.

This patent application may be related to U.S. patent application Ser. No. 13/964,490, titled "HEART MONITORING SYSTEM USABLE WITH A SMARTPHONE OR COMPUTER," filed Aug. 12, 2013, which is a continuation of U.S. Pat. No. 8,509,882, titled "HEART MONITORING SYSTEM USABLE WITH A SMARTPHONE OR COMPUTER," filed on Jun. 8, 2010, and to U.S. patent application Ser. No. 13/108,738, titled "WIRELESS, ULTRASONIC PERSONAL HEALTH MONITORING SYSTEM," filed on May 16, 2011, and published as US-2011-0301439, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This patent application discloses inventive concepts related generally to guiding, correcting, and/or improving the placement of electrodes on a subject/patient.

BACKGROUND

Electrical measurement of biological activity, and particularly non-invasive electrical measurement, is increasingly important in medical therapy, diagnostics, and research. For example, electrodes of various types may be used to record electrocardiograms (ECGs), electroencephalograms (EEG), electromyogram (EMG), galvanic skin reflex (GSR), electrooculogram (EOG), bioimpedance (BI), and others, including invasive or implantable measurements. Accurate and reliable electrical measurements from patients may require precise or consistent placement of the electrodes used for measurement on the patient's body, which may require that the user placing the electrodes have a great deal of training and experience. The consequences of placing the electrodes outside of the predetermined, conventional, or standard locations on the body may result in inaccurate results.

For example electrocardiography is used to examine and monitor the electrical activity of the heart. ECGs are increasingly valuable tools for treating patients at risk for heart disorders. Electrocardiograms (ECG) can be recorded or taken using multiple electrodes placed on the skin of a patient, and electrical signals recorded between two electrodes may be referred to as leads. A variety of different lead patterns, including different numbers of electrodes, may be used to take an ECG. For example, an ECG may be taken with 3, 5, and 12 leads. For a standard 12-lead ECG, 10 electrode positions are typically used: six on the chest, and one on each of the patient's arms and legs.

The placement of the electrodes for the ECG is important. Despite the common use of ECGs within the medical profession, it is not uncommon for electrodes to be incorrectly placed on the patient by the nurse, medical technician, or physician. Incorrect placement of electrodes can adversely affect the ECG results and make comparison of the ECG results to standard ECG data difficult. Because of this sensitivity, the placement of leads is typically left to trained medical technicians (e.g., ECG technicians), as it is difficult for an untrained user to correctly place electrodes; it would be particularly difficult for an untrained user to correctly place leads on their own body. As mentioned, placing one or more of the electrodes used to measure an ECG outside of the accepted (standard or conventional) positions on the patient's body can affect the ECG, making it difficult to compare to a standard ECG and therefore difficult for a medical professional to interpret.

Electrodes are typically placed on a patient by a human, allowing an opportunity for human error to result in incorrect electrode placement. The methods, devices and systems disclosed herein can be used to improve guide the electrode placement on a patient. Accurate electrode placement can result in improved patient data (e.g., ECG data), better patient diagnosis and treatment, and improved patient health. Although attempts have been made to minimize the error introduced by varying electrode placement in ECG systems, including creating systems that are supposed to tolerate a greater variability in ECG measurement, these efforts have had limited success. For example, U.S. Pat. No. 6,282,440 describes methods for calculating and determining whether electrodes are in the standard ECG electrode placement, an alternative electrode placement, or an incorrect electrode placement based on an analysis of the ECG measurements resulting from electrode placement. Unfortunately, U.S. Pat. No. 6,282,440 does not provide a method for guiding the initial placement of electrodes or easily correcting incorrect measurements.

Different configurations for ECG electrode placement may be used on a patient. Common, customary or standard positions for these ten electrode positions have been determined for use in taking a 12-lead ECG. Measurement taken from ten (10) electrode positions on a patient may be used to produce a standard 12-lead electrocardiogram (ECG).

Thus, a standard or conventional 12-lead ECG configuration typically uses 10 electrode positions, which may mean the placement of ten separate electrodes in these positions. FIG. 1 illustrates placement of 10 electrodes that may be used for a 12-lead ECG, with 6 electrodes on the patient's chest and one electrode on each of the patient's arms and legs. The electrode placed on the right arm is typically referred to as RA. The electrode placed on the left arm is referred to as LA. The RA and LA electrodes are placed at approximately the same location on the left and right arms, preferably near the wrist. The leg electrodes can be referred to as RL for the right leg and LL for the left leg. The RL and LL electrodes are placed on the same location for the left and right legs, preferably near the ankle. In practice placement of the arm and leg electrodes is much less challenging than placement of the electrodes on the patient's chest. Further, ECG measurements may be more sensitive to variations in the placement of chest electrodes.

FIG. 2 illustrates standard placement positions of the six electrode positions on the chest, labeled $V_1$, $V_2$, $V_3$, $V_4$, $V_5$, and $V_6$. For a standard 12-lead ECG measurement, $V_1$ is typically placed in the fourth intercostal space, for example between ribs 4 and 5, just to the right of the sternum. $V_2$ is placed in the fourth intercostal space, for example between ribs 4 and 5, just to the left of the sternum. $V_3$ is placed between electrodes $V_2$ and $V_4$. $V_4$ is placed in the fifth intercostal space between ribs 5 and 6 in the mid-clavicular line. $V_5$ is placed horizontally even with $V_4$ in the left anterior axillary line. $V_6$ is placed horizontally even with $V_4$ and $V_5$ in the mid-axillary line. Electrodes are also typically positioned on the patient's right and left arm and right and left leg. This arrangement of electrode positions, including the positions on arms and legs, may be referred to as standard or conventional 12-lead ECG electrode positions.

Based on measurements between these electrode positions, standard "lead" measurements may be taken. For example, lead I is the voltage between the left arm (LA) and right arm (RA), e.g. I=LA−RA. Lead II is the voltage between the left leg (LL) and right arm (RA), e.g. II=LL−RA. Lead III is the voltage between the left leg (LL) and left arm (LA), e.g. III=LL−LA. Wilson's central terminal (WCT or $V_w$) can be calculated by (RA+LA+LL)/3. Augmented limb leads can also be determined from RA, RL, LL, and LA. The augmented vector right (aVR) is equal to RA−(LA+LL)/2 or −(I+II)/2. The augmented vector left (aVL) is equal to LA−(RA+LL)/2 or I−II/2. The augmented vector foot (aVF) is equal to LL−(RA+LA)/2 or II−I/2. Leads I, II, III, aVR, aVL, and aVF can all be represented on a hexaxial system illustrated in FIG. 3. Incorrect or shifted electrode placement can shift the results of the ECG on the hexaxial system.

The signals from this 12-lead system may be used to examine the electrical signal resulting from cardiac activity. The 12-lead measurements have been accepted as providing medically relevant information about cardiac health. FIG. 4 illustrates a sample ECG annotated to show characteristic features used for analysis of cardiac function, in particular PQRST waves. Identification and measurement of the PQRST waves across the 12 leads is well accepted as providing relevant information about the health of a patient. For example, FIG. 5 illustrates data collected from a patient using a 12-lead standard configuration. The data can be analyzed to obtain representations of the PQRST waves for this patient. As mentioned, incorrect placement of the electrodes changes the measured values for the leads.

There may be multiple acceptable positions (or ranges of positions) for electrodes, including ECG electrodes. For example, FIGS. 6A and 6B show different configurations for the arm and leg electrodes that may be used in an ECG. The RA/LA electrodes may be placed near the wrist, as shown in FIG. 6A, or near the shoulder, as shown in FIG. 6B, and the RL/LL electrodes may be placed near the ankle (FIG. 6A) or near the pelvis (FIG. 6B). Positioning the arm electrodes near the wrist and the leg electrodes near the ankles as shown in FIG. 6A is widely accepted as a standard or conventional electrode configuration for the arm and leg electrodes in a 12-lead ECG. Alternatively, positioning the arm and leg electrodes adjacent to the thorax as shown in FIG. 6B may be referred to as the Mason-Likar system for electrode placement. The Mason-Likar system is often used to take an ECG during exercise because the arm and leg electrodes are positioned closer to the chest and torso and placed in areas of the body that move less during exercise. The electrode positioning differences between the standard configuration and the Mason-Likar system can result in differences in the ECG signals received, since the relative positioning of the arm electrodes affects the measured leads (see, e.g., "Resting 12-Lead ECG Electrode Placement and Associated Problems" by Macfarlane et al., SCST Update 1995).

Thus, it would be beneficial to provide improved methods for accurately placing electrodes on the body of a patient.

SUMMARY OF THE DISCLOSURE

In general, described herein are methods, devices and systems for guiding and/or correcting placement of electrodes on a patient. These methods may be particularly useful for guiding placement of electrodes for ECG measurements. In general, the systems, devices and methods described herein process a picture of a patient to output electrode positions on the patient. Typically this may include presenting an image of the patient (e.g., a modified version of the picture of the patient) showing the locations for the electrodes relative to the actual patient picture.

For example, a system or device for guiding electrode placement as described herein may include control logic for controlling a processor (e.g., microprocessor of a computing device such as a hand-held computing device) to receive a picture of a patient, to analyze the patient to determine the correct placement of the electrodes, and to output an image of the patient on which the correct predetermined electrode positions have been marked. In general, the control logic may be configured as software, hardware or firmware, and may control a general-purpose computing device (e.g., computer, tablet, or the like) or a mobile telecommunications device (smartphone, such as Iphone™, Android™, etc.) to accept or acquire the picture and output the image of the patient. The processing step may be performed remotely or locally. In general, the processing step may include comparing the picture of the patient to a database (e.g., an electrode placement database) of various body types and corresponding predetermined, conventional or standard positions for electrodes associated with each body type. The picture of the patient may also be normalized prior to comparing the picture the patient database by adjusting the size, and/or in some cases the aspect ratio, brightness, contrast, or other image features, of the picture to allow direct comparison with the database. Normalization may be performed using a marker included as a part of the picture. For example, the picture of the patient may be taken with a marker of known or knowable size on the patient, and the marker may be used as a normalization marker to normalize the picture before comparison with the database. Normalization may also be performed to even out the brightness, contrast, sharpness, or other imaging quality of the picture. The marker may be placed or applied directly onto the patient (e.g., the patient's torso), e.g., by adhesive, etc.)

Also described herein are methods performed by the devices and systems for guiding electrode placement, such as methods of guiding electrode placement on a patient.

For example, described herein are methods for guiding proper placement of electrodes on a patient that include: comparing a picture of the patient to an electrode placement database to determine positioning of electrodes on the patient, wherein the electrode placement database comprises representations of a plurality of body types and predetermined electrode placement positions corresponding to each body type; and presenting an image of the patient showing positions for electrodes on the image of the patient.

These methods may be particularly adapted for guiding placement of ECG electrodes on a patient in a standard or conventional configuration on the patient. Thus, the database may be configured to include a plurality of body types with corresponding conventional/standard electrode placement positions for each body type in the database.

In some variations electrode positions may be determined and indicated for all of the electrodes (e.g., all 10 electrode positions used for a standard 12 electrode lead). However, in some variations on a subset of the electrode positions may be determined and/or displayed. For example, a method of guiding positioning of a standard/conventional 12-lead electrode placement may determine and show only the six electrode positions on the patient's chest. In some variations where other electrode positions may be determined relative to one or more key electrode positions, only the position of the key electrode(s) may be shown.

In general, any appropriate picture of the subject may be used. In some variations, the system, devices or methods may include taking or acquiring the picture. As described in greater detail below, in some variations the picture may be taken by the system or device performing the method (e.g., a smartphone or other handheld computer device). The systems, devices and methods described herein may instruct a user how to take the picture of the patient, including positioning the patient (facing forward, standing, sitting, lying, etc.), approximately how far from the patient to take the picture, positioning a normalization marker on or near the patient, and the like. The picture may be received as a digital image. The picture may include an image of the patient, and particularly a region of the patient's body to which the electrodes are to be applied. For example, when applying ECG electrodes, the picture may include the patient's torso or chest. Additional regions of the patient's body may be included, such as the patient's head, legs, etc. The patient may be standing, seated or lying down. The region of the patient to which the electrodes will be applied is typically bare (e.g., a may be shirtless or at least partially shirtless, so that the skin can be visualized). As mentioned, in some variations a normalization marker may be included as part of the picture. For example, a reference marker may be placed on the patient; the reference/normalization marker typically has a known or standard size, such as a coin (e.g., a U.S. quarter, penny, etc.). In some variations the reference marker is provided, and may be a distinct shape or color. In some variations the marker is automatically recognized by the apparatus. For example, the marker may include a readable code (e.g. bar code, alphanumeric code, QR code, etc.); alternatively the apparatus may identify the marker by color, shape, etc.

In variations in which the method, system or device guides the user through taking or acquiring the picture, the picture may be qualified by the system or device. Qualifying the picture may include checking the picture to confirm that it is suitable and can be analyzed (e.g., compared) to the database.

As used herein the phrase "patient" is intended broadly to include any subject on whom the methods, devices and systems may be used to help position electrodes. A patient may include an animal (in systems and devices specifically configured for use with that type of animal) or human, and may include healthy or non-healthy subjects. As used herein a "user" may be a person using the systems, methods and devices as described herein. In some variations the user is the same as the patient, as the systems, devices and methods described herein may be used by a patient to guide placement of electrodes on his or herself.

In some variations, comparing the picture to the electrode placement database may comprise determining the standard placement of electrodes for a 12-lead ECG on the patient.

In general, comparing the picture of the patient to the electrode placement database may include determining a match (e.g., the closest match) between the picture and one or more representative body types in the patient database. Once one or more closely matching representative body types have been identified, the electrode placement corresponding to the representative body types for the match(es) may be mapped to the picture of the patient. Where more than one match is identified, electrode placement may be determined from the standard electrodes placements corresponding to the multiple representative body matches by weighting, averaging, or other appropriate statistical method for finding a consensus standard among the closest matches, and mapping this standard electrode placement to the picture of the patient.

As described in greater detail below, an electrode placement database typically includes a plurality (e.g., >10, >100, >1000, >10,000, etc.) of representations of standard/conventional electrode placement for different bodies. A representation of a body type may include an image of a body (e.g., picture, portion of a picture, etc.) or information extracted from an image of a body including electrode placement specific for that body, where the electrode placement has been confirmed or verified as within the standard/conventional bounds. The various body types may include body types of different shapes and sizes (height, weight, morphology), gender (male/female), age (infant, child, adult, elderly), physical morphology (shoulder width, chest size, waist size, etc.), and the like. Each body type representation may be unique, although similar body types may be included, creating clusters of body types around more common body types. All of the body types in the database may be pre-normalized to allow comparison between the different representations. Multiple different electrode placement databases may be used. For example, separate databases may be used for different patient positions (lying, sitting, standing, etc.), or for different patient genders, ages, etc. Further, different electrode placement databases may be used for different standard/conventional electrode placements.

Thus, in addition to normalizing the picture before comparing it to an electrode placement database, the picture may be processed to prepare it for comparison with the database. In variations in which the comparison is made by extracting features from the picture and comparing these extracted features to the representations of body types in the database, the extraction of features may be performed on the picture before (or as part of) the comparison. For example, when comparing the picture of the patient to the electrode placement database includes determining anatomical landmarks from the picture and comparing the anatomical landmarks to the electrode placement database, anatomical landmarks may be extracted from the picture first. The picture may also be processed to remove patient-identifying features (e.g., all or part of the patients face, etc.) which may be relevant to protect patient privacy.

As mentioned above, the comparison of the picture with the database may comprises interpolating between the closest matches to the picture and two or more representative body types in the patient database.

In some variations, comparing the picture of the patient to the database comprises using pattern recognition to determine the closest match between the picture and a representative body type in the database. In some variations, comparing the picture of the patient to the electrode placement database comprises comparing the normalized picture of the patient to the electrode placement database.

The methods, devices and systems described herein may also include presenting the image of the patient showing positions for electrodes on the image of the patient. Any appropriate image of the patient may be presented, including a modified version of the picture of the patient showing the positions of the electrodes determined by comparison with the database. In some variations, the image of the patient is digitally displayed (e.g., on the handheld computing device). And may be enlarged (zoom in/out) or manipulated so that the user can see where to place the electrodes. In some variations the image may include additional guidelines, including measurements (rulers, distances in inches, mm, etc.) relative to the patient, including patient landmarks, such as anatomical landmarks, and/or relative to other electrodes.

The presentation of the image of the patient showing the conventional/standard position of the electrodes may show all of the electrodes, or some of the electrodes. In some variations, the presentation of the image may include a series of images separately showing the patient with different electrode positions indicated, to better allow a user to step through the process of applying or repositioning the electrodes. In general, the presentation of the image of the patient may be visual (showing the image) and may also include textual (written/spoken) instructions for applying the electrodes. For example, in variations of the systems and methods described herein intended for use with a handheld computer device, such as a smartphone, the device may controlled to step the user through both taking the patient's picture and positioning (or repositioning) the electrodes by looking at the screen of the smartphone.

In some variations, the methods, devices and systems described herein may be used to correct and/or verify the position of electrodes already present on a patient. For example, the user may take or receive a picture of a patient with ECG electrodes already on the chest. Comparing the picture of the patient to the electrode-placement database may also compare the position of the electrodes already on the patient with the determined standard/conventional positions. Thus, comparing the picture of the patient to an electrode placement database may comprise comparing a picture of the patient having one or more electrodes already placed on the patient's chest to the electrode placement database. The position of the one or more electrodes already placed on the patient's chest may then be verified either automatically (indicating when one or more is incurred) or passively by overlying the correct positions (indicated in some specific way, e.g., by a color) onto the picture of the patient to form the presented image. In some variations the image presented includes an image of the patient showing corrected positioning of electrodes on the image of the patient.

Also described herein are methods for guiding placement of ECG electrodes that include: receiving a picture of a patient including the patient's chest; comparing the picture of the patient to an electrode placement database to determine positioning of electrodes on the patient, wherein the electrode placement database comprises representations of a plurality of body types and predetermined conventional ECG electrode placement positions corresponding to each body type; and presenting an image of the patient showing positions for conventional ECG electrode positions on the image of the patient. The method, wherein comparing the picture of the patient to the electrode placement database includes determining the closest match between the picture and a representative body type in the electrode placement database.

As mentioned above, comparing the picture of the patient to the electrode placement database includes determining anatomical landmarks from the picture and comparing the anatomical landmarks to the electrode placement database. In some variations, comparing the picture of the patient to the database comprises using pattern recognition to determine the closest match between the picture and a representative body type in the electrode placement database.

In any of the variations described herein, the comparing of the patient picture with the electrode placement database may be performed remotely from the other steps. For example, a smartphone may be used (e.g., using an application downloaded to the phone) to acquire the picture of the patient, and to present the image of the patient showing the conventional positions of the electrodes; the comparison of the picture with the database may be performed remotely, using a remote server. Thus, the database may be maintained separately from the application on the smartphone (or other device). This may allow modification, updating, or otherwise amending the database and/or the mechanisms for comparing the picture of the patient to the database. The image generated may then be presented on a handheld computer device after it receives information (or the generated image) back from the remote database. Alternatively, in some variations all of the steps are performed on the local level (e.g., using the handheld computing device, such as a smartphone or tablet computer).

As mentioned above, the picture of the patient may include a normalization marker. Thus the step of receiving the picture of a patient may include receiving a picture of a patient includes a normalization marker. In some variations, the picture of the patient received may include electrodes on the patient's chest; the method, device or system may verify the placement of the electrodes already on the chest relative to conventional ECG electrode placement positions.

Also described herein are methods for determining the placement of ECG electrodes including: receiving a picture showing a patient including and a normalization marker; normalizing the picture using the normalization marker; comparing the normalized picture to an electrode placement database comprising representations of a plurality of body types and predetermined ECG electrode placement positions for each body type to determine positioning of electrodes on the patient; and presenting an image of the patient showing positions for ECG electrodes on the image of the patient.

A system or device may be configured to perform any or all of the steps described above for receiving a picture of a patient including the region of the patient to which electrodes are to be applied, analyzing the picture, and providing an image of the patient (or any other patient-specific map) showing the location(s) of one or more electrodes on the patient based on predetermined, conventional and/or standard electrode positions.

Although many of the examples described herein are specific to systems, devices and methods of placing ECG electrodes according to standard or convention 12-lead ECG electrode placement, these systems, devices and methods may be used (or adapted for use) with any predetermined, conventional and/or standard electrode positioning system, including electrodes for electroencephalograms (EEG), electromyogram (EMG), galvanic skin reflex (GSR), electrooculogram (EOG), bioimpedance (BI), etc. For example, the electrode placement database may include a variety of body types and corresponding predetermined, conventional and/or standard electrode positions for each of the body types for EEG, EMG, GSR, EOG, BI, etc. In some variations, the different electrode placement regimes (different conventional and/or standard electrode placement) may be linked in the database to each body type, and a user may select which placement regime to display. In other variations, more than one placement regime may be shown, either sequentially or simultaneously, for the same patient. For example, for ECG electrode placement, the electrode placement can correspond to 3-lead, 5-lead, and 12-lead ECGs.

A system for guiding electrode placement may generally include control logic, which may be executed as software, hardware, or firmware (or combinations thereof) that receive the picture of the patient, determine conventional and/or standard electrode placement for that patient using an electrode placement database, and output a map or image of the patient showing where on the patient the electrodes should be positioned. The system may also be configured to guide or walk the user through the process of taking the picture of the patient and/or positioning the electrodes on the patient. In some variations, the system is configured to guide the user by audible instructions, written instructions and/or visual instructions. The system may be configured to work from (e.g., control) a handheld computing device, including a smartphone (e.g., iPHONE, ANDROID, etc.) to receive (and in some cases take) the picture of the patient and output the image of the patient with the determined electrode position(s) marked. For example, the system may be configured as an application for a smartphone that is downloadable onto the smartphone.

Any of the systems described herein may be dedicated systems that come pre-configured to receive a patient picture and output an image of the patient showing electrode placement positions, and do not require downloading of an application (e.g., software) onto a separate device. For example, a system may include a camera for taking a picture of the patient, control logic for receiving the picture, controlling analysis of the picture to determine electrode placement using an electrode placement database, and outputting a map or image of the patient showing the location of one or more electrodes according to a conventional and/or standard electrode positioning regime. The system may include all or a portion of the electrode placement database, or the system may communicate with a remote electrode placement database. Further, the system may include a comparison unit, which may include comparison logic for comparing the picture of the patient with the body types in the electrode placement database in order to find one or more close matches between the patient and the body types in the database, from which the predetermined conventional and/or standard electrode positions can be extrapolated to the patient picture.

The system may also be configured to use (and may include as part of the system) a normalization marker that is included in the picture of the patient. A normalization marker is typically a distinct maker that the systems/devices described herein may distinguish in the picture, and which may be used to provide scale and/or orientation for reference in the picture. For example, the normalization marker may be a sticker that can be attached to the skin of the patient; the sticker may be brightly colored, and may have a known size (e.g., an orange circle of one inch diameter). The system/device can therefore distinguish this sizing marker in the picture, and can normalize the picture using the normalization marker. In some variations the normalization marker may also provide a reference position which the system may use in providing instructions for placement of the electrode(s). In some variation more than one sizing maker may be used. A normalization marker may be a common object of known dimension, such as a coin. The user may indicate in the system/device what the normalization marker (e.g., from a menu of possible normalization markers).

As mentioned, the image of the patient showing positioning of electrodes can be presented to the user on a handheld computer device. For example, the handheld computer device can be a mobile phone, smartphone, tablet computer, or camera with network connectivity.

DETAILED DESCRIPTION

Figure 1:
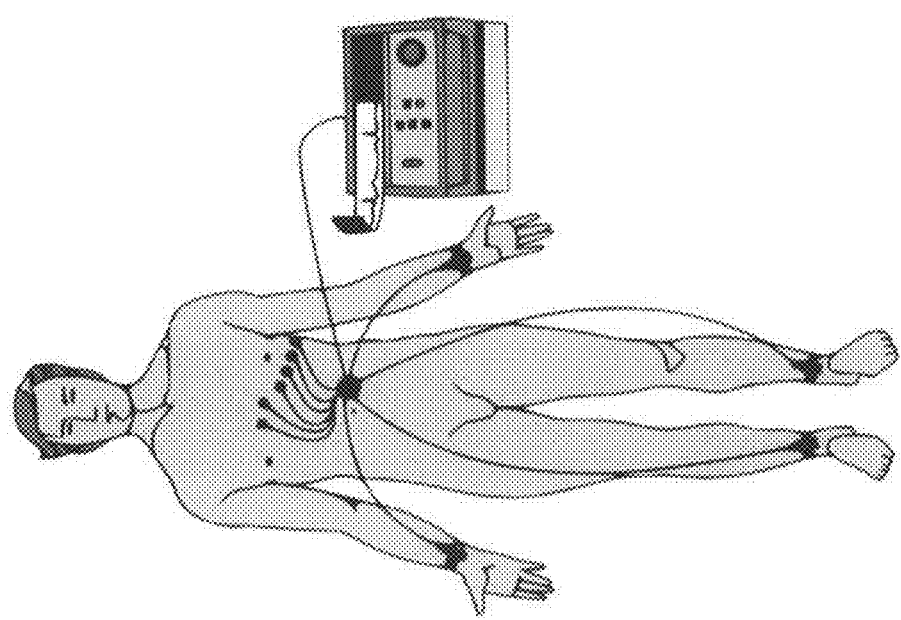
FIG. 1 is a pictorial representation of a body showing an example of electrode placement for taking an ECG.
Figure 2:
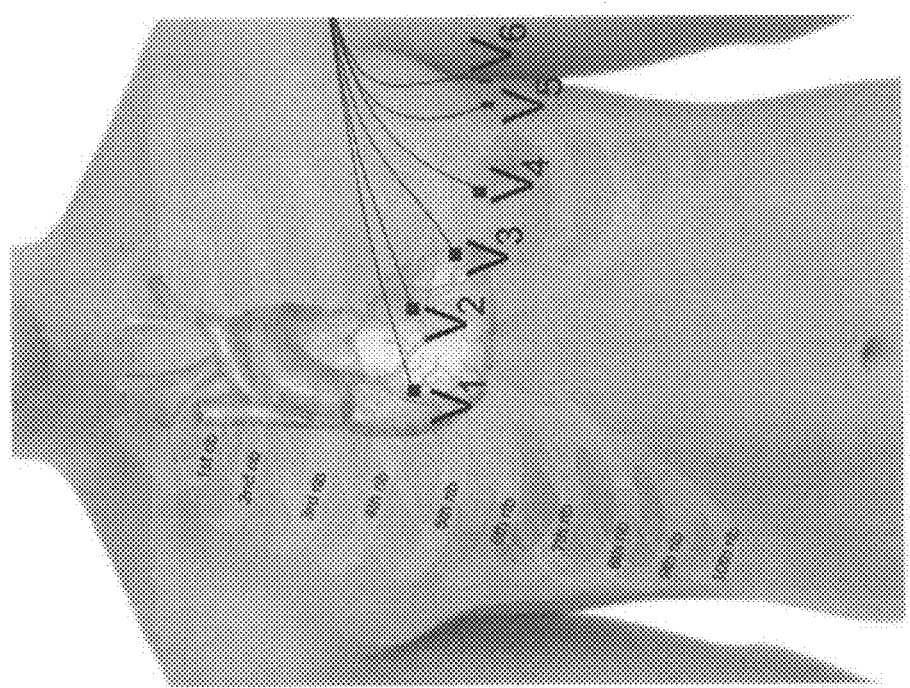
FIG. 2 shows a semi-transparent image of a chest showing one example of electrode placement on the chest for taking an ECG, according to a portion of a conventional 12-lead ECG electrode placement (electrode positions on the arms and legs are not shown).
Figure 3:
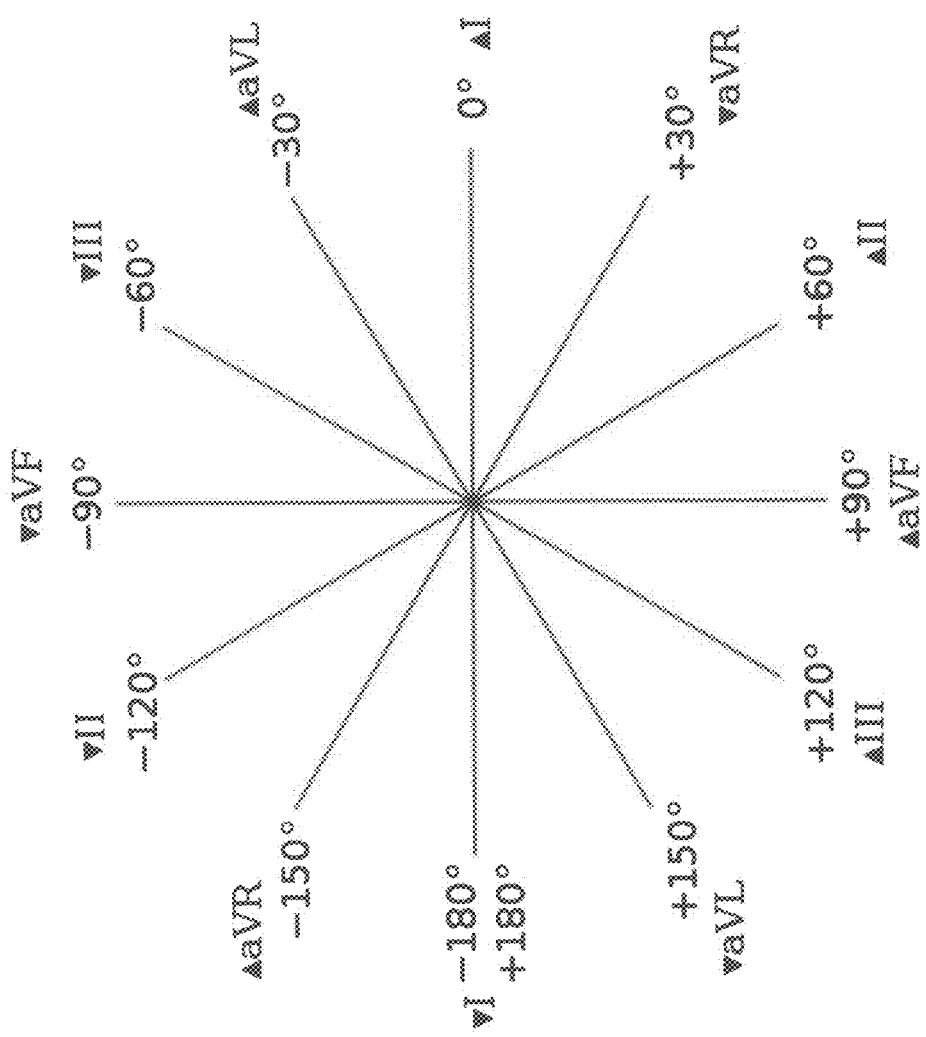
FIG. 3 shows a hexaxial reference system for an ECG.
Figure 4:
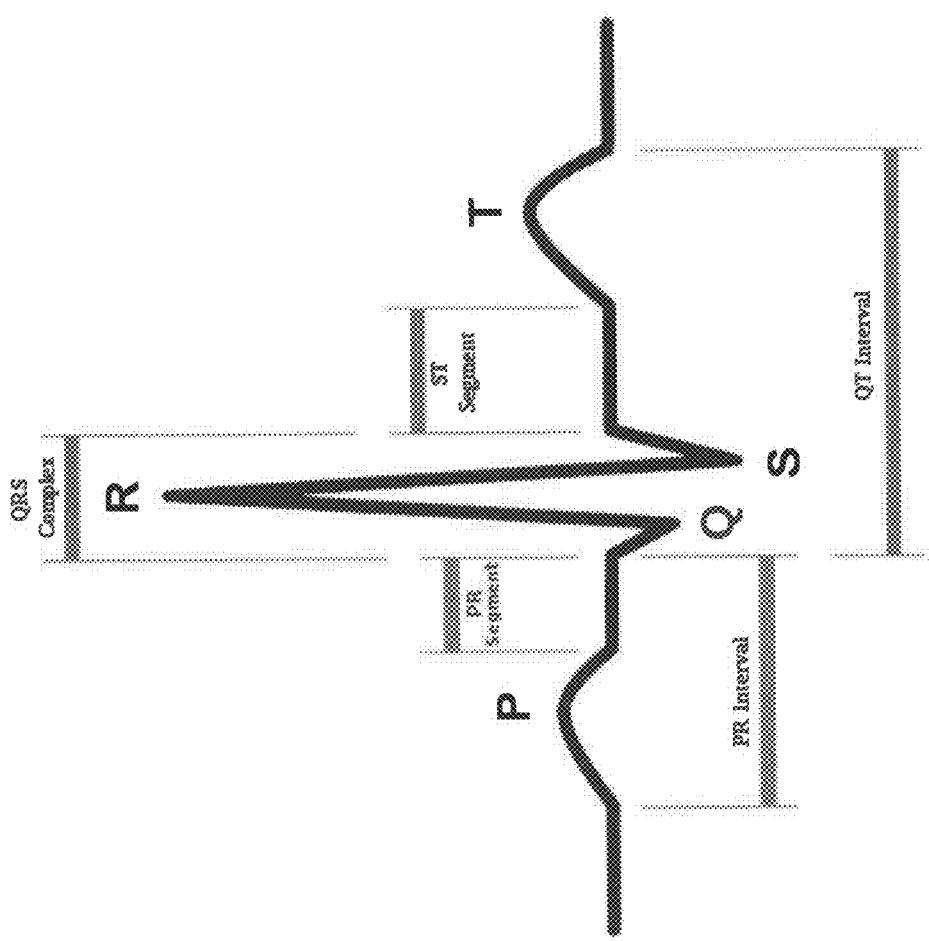
FIG. 4 shows an exemplary ECG trace illustrating the PQRST wave.
Figure 5:
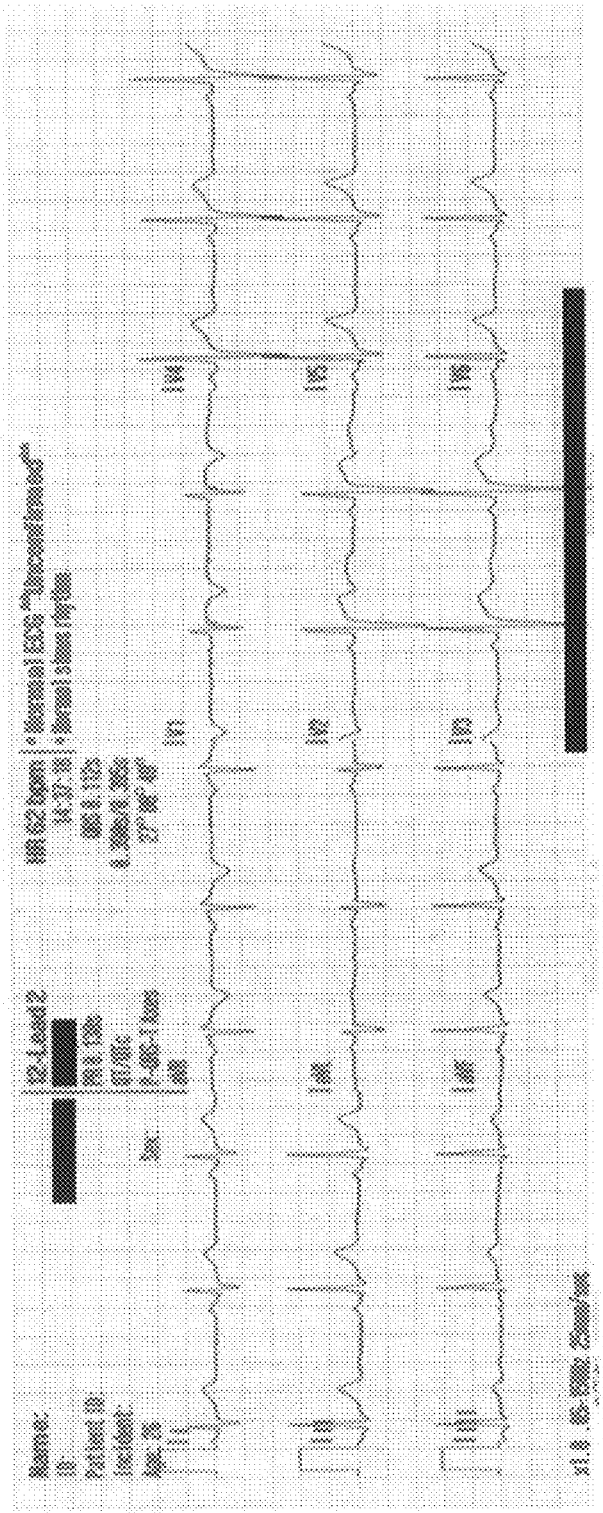
FIG. 5 shows a sample 12-lead ECG for a patient.
Figure 6B:
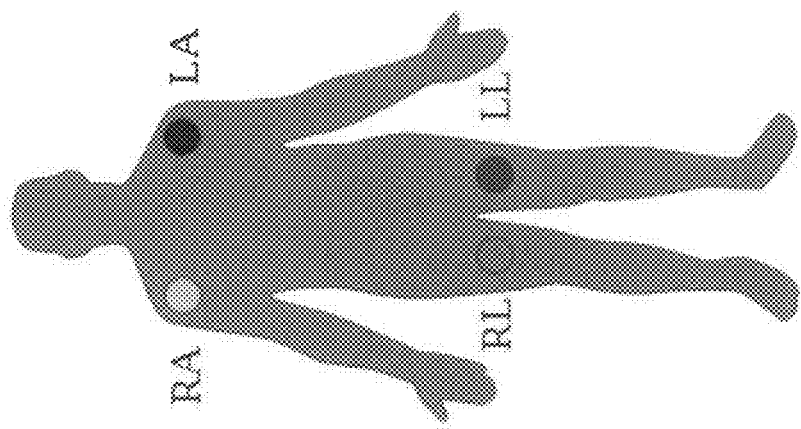
FIGS. 6A and 6B show conventional/standard and Mason-Likar arm and leg electrode placements respectively, for ECG electrode placement.
Figure 6A:
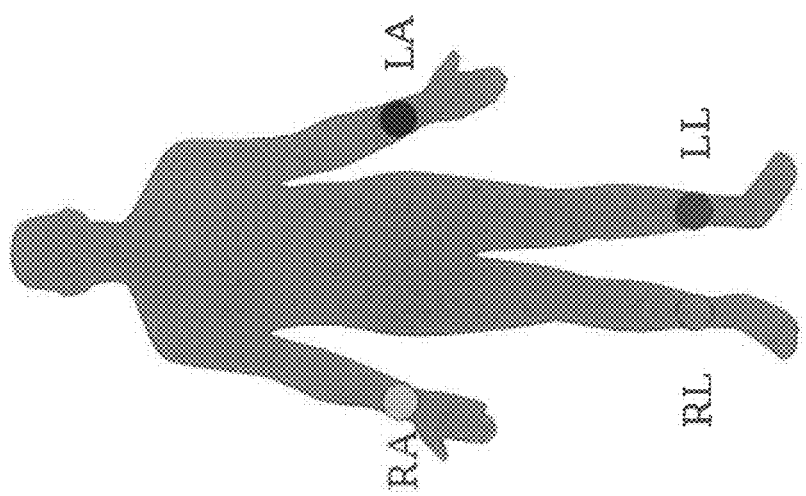

In general, described herein are systems, devices and methods for determining the placement of electrodes on a patient. In general, these system, devices and methods operate by receiving a picture of a patient's body, and comparing the picture to a database with representations of a plurality of different body types, in order to find the closest match or matches between the patient picture and the different body types. The database may be referred to as an electrode placement database, and typically includes representations of a variety of different body types and, for each body type, associated predetermined electrode placement positions for each of the body types. The predetermined electrode placement positions may correspond to conventional and/or standard electrode positions, which may have been previously verified. These systems, devices, and/or methods may then extrapolate the optimal placement of one or more electrode(s) on the picture of the patient based on the one or more matches from the database, and present a map of this optimal placement. The map may be an image that includes the picture of the patient on whom the optimal position(s) (or a range of positions) have been drawn. These systems may be referred to as systems for guiding electrode placement (or electrode placement systems); similarly the devices may be referred to as devices for guiding electrode placement or electrode placement devices; and the methods may be referred to as methods for guiding electrode placement. These systems, devices and methods may be particularly helpful for assisting, confirming or guiding placement of ECG electrodes, e.g., for performing "standard" 12-lead ECG measurements.

Any of the systems described herein may be configured for operation with a handheld computing device, and particularly a smartphone device such as an ANDROID or iPHONE. Thus, the steps of receiving the picture of the patient, and/or presenting the image showing electrode locations may be performed by a handheld computer device. Thus, in some variations the systems described herein generally include control logic for directing the handheld computing device to perform the steps of acquiring the picture of the patient, analyzing the picture using the database, and presenting the image of the patient. The control logic may also include additional steps, at least some of which may be optional, including guiding a user to acquire the picture of the patient, using a normalization marker (which in some variations may be referred to as a sizing marker), normalizing the picture, passing the picture to an analysis unit for accessing an electrode placement database and comparing the picture to the database, extrapolating the optimal electrode placement for the patient from the database, and generating a placement map (e.g., image) for the patient. The control logic may also present the placement map.

For example, the methods, systems and devices described herein may be used to determine the optimal placement of electrodes for performing 12 lead ECG recordings from a patient by receiving a picture of a patient's body showing the patient's chest and outputting an image of the patient showing optimal positions for at least some of the electrodes on an image of the patient. Thus, the determined electrode positions can correspond to conventional lead positioning for electrodes in an ECG in a 12-Lead ECG, and may be used to position electrodes in the proper positions on the patient's actual (rather than virtual) chest.

Examples and illustrations of these methods, devices and systems are provided herein, however the inventions described herein are not limited in application to the specific details of construction, experiments, exemplary data, and/or the arrangement of the components set forth. Other embodiments or variations for practicing or carrying out these inventions are expressly contemplated. The terminology employed herein is for purpose of description and should not be regarded as limiting, unless specifically indicated as such. Thus, in the following detailed description of embodiments of the disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

Figure 10:
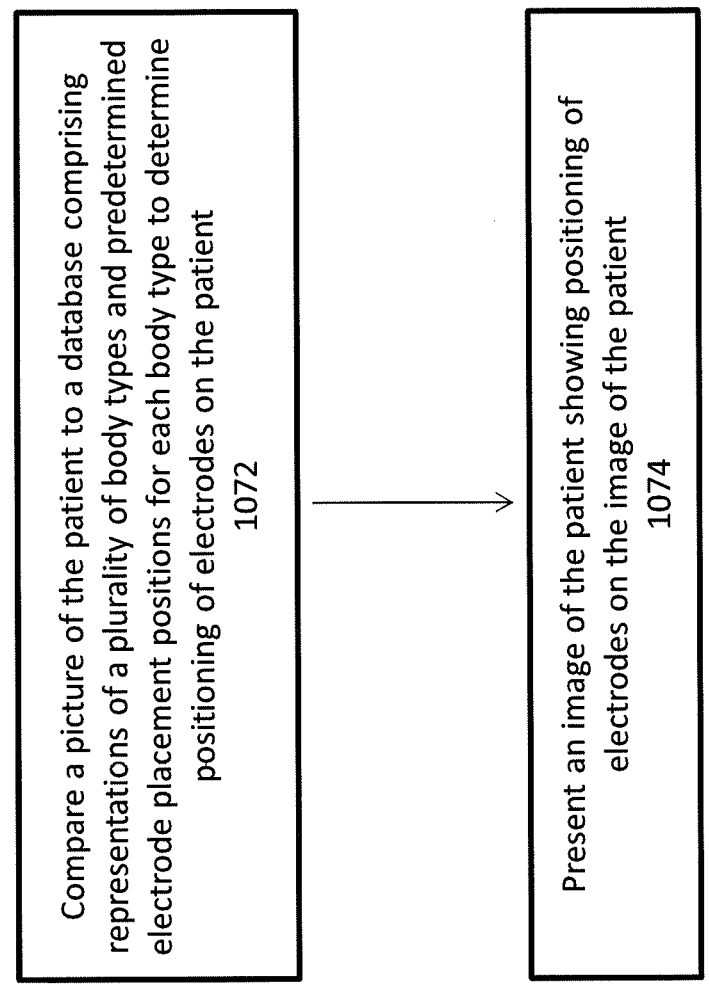
FIG. 10 is an exemplary flowchart describing a method for guiding the placement of electrodes on a patient in accordance with one embodiment.

As illustrated in FIG. 10, a method of guiding electrode placement may include comparing a picture of a patient to an electrode placement database that includes a plurality of predetermined, conventional and/or standard electrode placement positions for a variety of different body types 1072. The patient picture is compared to the variety of different body types to determine the closest match(es). The corresponding electrode placement positions on the one or more closest matches may then be used to extrapolate the conventional/standard electrode placement on the patient. The conventional/standard electrode placement may be presented in the form of an illustration of the patient showing positions for one or more electrodes based on the comparison with the database 1074.

Figure 7B:
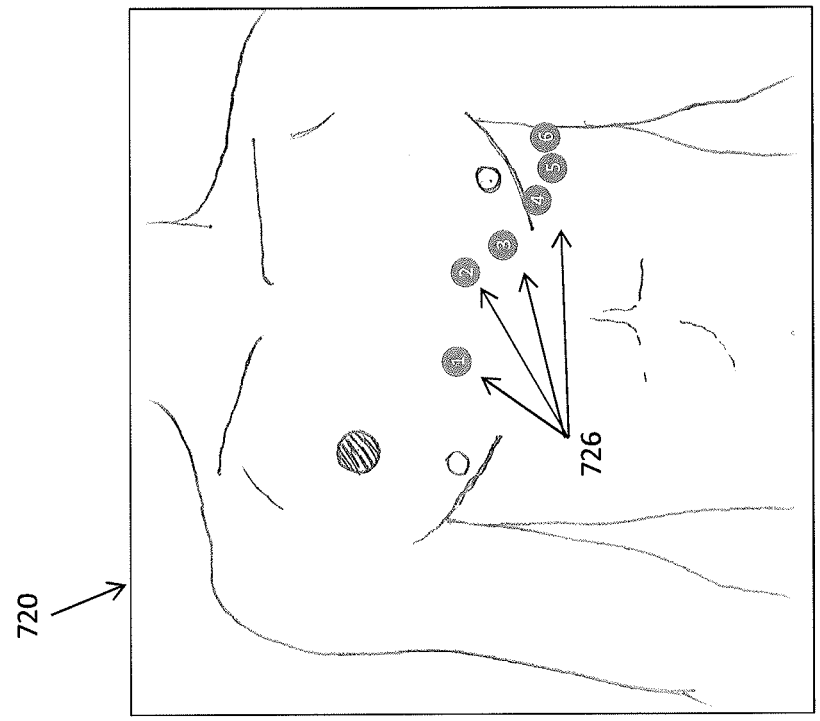
FIG. 7B shows an image of the patient from the picture of FIG. 7A onto which positions for six ECG electrodes have been marked as described herein.
Figure 7A:
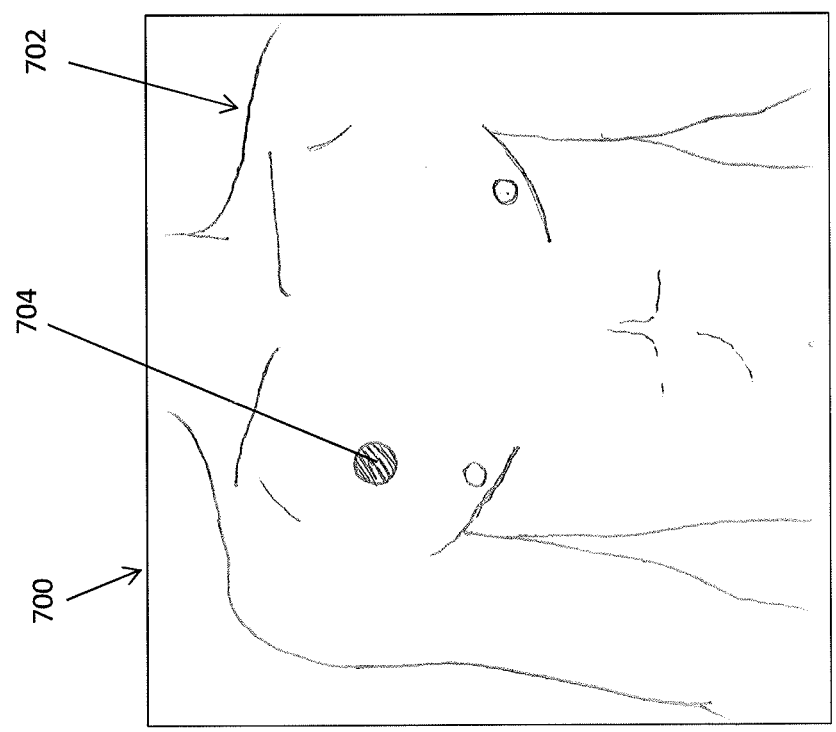
FIG. 7A shows one example of a picture of a patient onto which electrodes may be placed for a standard ECG electrode placement.

FIGS. 7A and 7B illustrate a procedure for guiding placement of a subset of ECG electrodes to make a conventional 12-lead ECG recording. FIG. 7A shows a picture 700 of a patient's chest (torso) 702 to which the ECG electrodes will be applied. This picture may be taken immediately before it is desired to apply (immediately before applying) the electrodes. The subject may be instructed to position themselves (or they may be positioned by a user) in a particular posture; for example, the subject may be asked to stand, sit, lie down, etc. The patient's posture may be matched to the posture of the body types in the electrode placement database.

In FIG. 7A, the picture is taken with the patient's shirt removed. The patient is standing, and their arms are down at their sides. A normalization marker 704 is included on the patient as well. The normalization marker may be any marker having properties that are known (or entered into) the system or device. In FIG. 7A the marker is a circular sticker that is placed on the upper right side of the patient's chest before taking the picture. The sticker has an approximately one-inch diameter. In some variations the maker is a common object of known dimensions that is placed or held by the subject while taking the picture. For example, a coin (e.g., quarter, nickel, penny, etc.) may be placed on the patient. As described in more detail below, the normalization maker may provide a reference to normalize the figures so that it can be directly compared with the electrode placement database.

The patient picture in FIG. 7A can then be compared to the electrode placement database to find a match with one or more of the body types in the database. In some variations, if no close match is found, a notification that the system/device cannot find a match or cannot provide positioning, may be provided. In any variation, the method and system may provide an indication of the confidence of the match/placement guidance, which may be based on how closely the patient picture matches body types in the database.

Once one or more matches is identified from the database, the predetermined conventional and/or standard electrode positioning for the one or more close matches may be used to suggest positioning of electrodes for the patient. For example, electrode placement positions may be extrapolated from the matching body type(s) and shown on the picture of the patient, as illustrated in FIG. 7B. In this example, six ECG electrode positions 726 are shown on the patient's picture. This image may be presented to the user to assist them in placing the electrodes on the subject. After placement, the patient's picture may be taken to confirm that the electrodes have been properly positioned, as illustrated in FIGS. 8A and 8B.

In general, electrode placement may be confirmed using the methods and systems described herein. FIG. 8A shows a picture 800 of a patient's torso 802 (similar to FIG. 7A), in which six electrodes (numbered one to six) have been positioned 816. This picture (which also includes marker 804) can be compared to an electrode placement database to generate an image 820 of the patient (including the actual electrode positions) onto which proposed electrode positions 826, 826' are also shown. In FIG. 8B, the conventional/standard electrode positions are overlaid onto the picture 800. Thus, the user may move or adjust the position of the electrodes as shown in the image 820. Although the technique illustrated above provides images of the patient showing corresponding conventional/standard electrode positions based on the database, in some variations the image of the patient showing the conventional/standard electrode positions determined from the database may be displayed on a video (including real-time display) of the patient, allowing real-time repositioning of the electrodes.

Figure 8B:
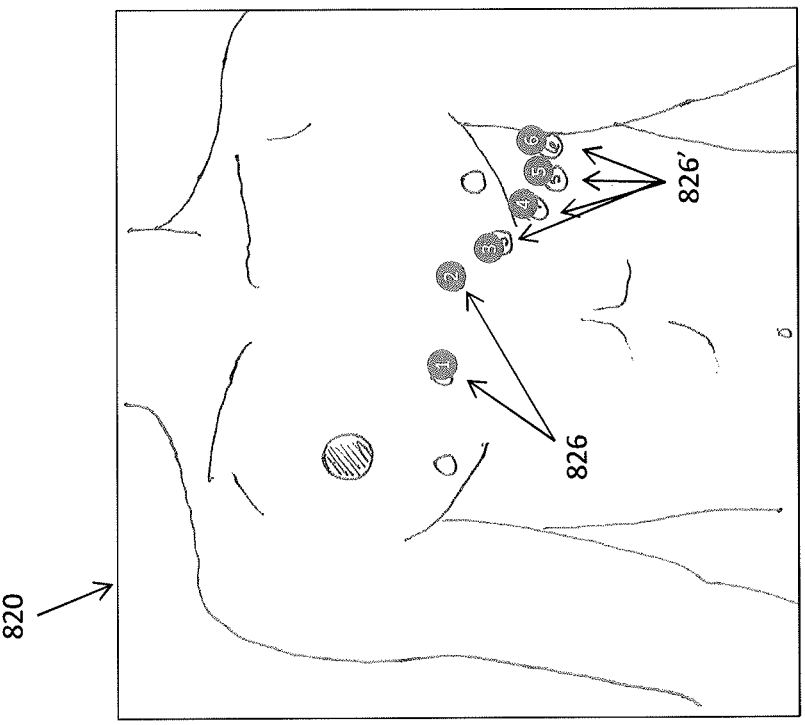
FIG. 8B shows an image of the patient (including the six electrodes) from FIG. 8A, onto which corrected positions for the six ECG electrodes have been marked.
Figure 8A:
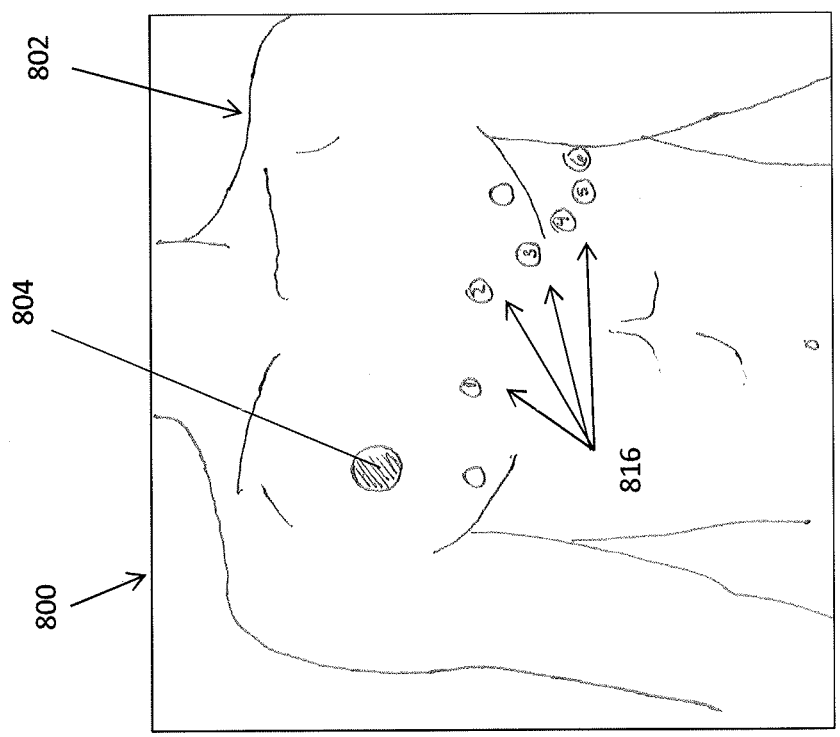
FIG. 8A shows a picture of a patient on whom six electrodes have already been placed.

For example, in FIG. 8B the suggested positions for the six ECG electrodes 826, 826' are slightly shifted from the positions of the actual electrodes 816 already on the patient's chest. In some variations, the suggested or proposed positions may be shown in a semi-transparent visual. In general, the proposed positions may be shown in a color. The outputted image may be enlarged by the user to help show the relative position of the proposed conventional/standard electrode positions. Although the majority of examples provided herein include an output image in which conventional/standard electrode positions are illustrated on a picture of the subject, in some variations, the output is an image of the closest match from the database, showing the correctly placed conventional/standard electrode positions on a body that is most closely similar to that of the patient.

The picture of the patient can be provided from any appropriate source. In some variations the picture is taken using a computer device with a camera or adapted for use with a camera, including the built-in camera. Examples of computer devices with cameras include smartphones, cell phones, laptop computers, tablet computers, digital cameras, and home computers adapted for use with a camera. The control logic controlling the handheld computing device may directly access the camera to take the picture, or it may access stored pictures, e.g., stored in a memory on the handheld computer, and allow the user to select the picture to be used. As mentioned, the system may guide the user to take and/or select the picture to use, including taking the picture with the normalization (e.g., sizing) marker visible. In general, the picture of the patient can be taken by a user or the patient. Examples of users include medical technicians, nurses, and doctors.

For example, the picture of the patient can be previously taken, e.g. stored on the computer device, and selected for comparison. The picture of the patient can be taken within an application and then selected for comparison. The picture of the patient can be previously taken and stored on a remote server and selected from a remote server for comparison.

The picture of the patient generally includes the region of the patient where the electrodes will be applied. For example when the method, devices or systems are for guiding a user to place or correct placement of ECG electrodes, the picture can include the chest of the patient. The picture of the patient can include electrodes already placed on the chest. The picture may therefore be taken or selected so that it shows the patient's bare (or relatively bare) chest. In some cases the patient's chest can be covered by clothing.

As mentioned above, the picture of the patient can include a normalizing marker. The marker (e.g., sizing marker) may have a known size. The marker can be used to normalize or standardize the picture of the patient prior to comparison with the database. For example, the marker may allow the picture to be normalized by scaling the picture based on the known size of the marker so that it approximates the size of the body types in the database. Other features may be normalized as well, including the brightness, contrast, focus, etc. of the picture using the known properties of the normalizing marker. A picture of a patient having a normalizing marker can be analyzed to normalize the sizing of the picture of the patient to size compare with the representations in the database. Thus, normalization or standardization of the picture of the patient can facilitate the comparison of the picture of the patient with the database containing information on predetermined electrode placement positions for a plurality of different body types.

The picture (an in some variations the normalized picture) of the patient is generally compared to an electrode placement database to determine one or more close matches between the patient picture and the exemplary or body types in the database, for whom conventional or standard electrode placement positions are known relative to each exemplary body type. Thus, an electrode placement database may include information on predetermined electrode placement positions for a plurality of different body types. The database can include representations for electrode placement for a plurality of different body types. In some variations, the representations of body types comprise images bodies including electrodes positioning in a predetermined, conventional and/or standard position for a particular electrode placement regime. In some variations the representations of body types includes information extracted from an image, such as anatomical landmarks for each different body type. Thus, the representations of different body types may include characteristic properties of each body type in the database (size, shape, etc.), with corresponding electrode placement information for that body. For example, distance and direction between the predetermined locations for the electrode placement and anatomical landmarks may form at least part of the database. The representations may be normalized each of the different patients included in the database. For example, an electrode placement database may include images of a variety of bodies with the electrodes shown on the body (a corresponding image without the electrodes present may also be included). The database can include a variety of different exemplary bodies, spanning a variety of different body types, weights, heights, genders, sizes, ages, body mass indexes, etc.

In some embodiments the database is stored on a remote server. In some embodiments the database can be stored on system or device (e.g., a handheld computer device) locally.

As mentioned above, the electrode placement database typically includes representations of a plurality of different body types that can be compared against a patient picture (or against descriptive information extracted from the patient picture), and each body type has a corresponding predetermined, conventional and/or standard electrode(s) position for that body type. As used herein, a body type refers to an exemplary body, which may include characteristic shape, size, gender, position, etc. The corresponding predetermined, conventional and/or standard electrode(s) position may be verified for that body type by an expert trained in positioning the electrode(s) for the electrode placement regime of the database. For example, an electrode placement database for placing ECG electrodes in a conventional 12-lead ECG pattern may include a number of images of "model" body types each of which has a verified arrangement of electrodes in the predetermined, conventional and/or standard electrode(s) position for a 12-lead ECG. Thus, these model body types may correspond to images of subjects having conventionally placed 12-lead ECG electrodes. The placement for each model body type may be confirmed by an expert in placing electrodes in for 12-lead ECG measurement.

A database may include any number of model body types. For example, in some variations the database includes more than 100 model body types; more than 500 model body types; more than 1000 model body types; more than 2000 model body types; more than 5000 model body types, etc. The same subject may provide more than one model body type in the database, since different body positions (e.g., sitting, standing, lying down, etc.) or different angles (oblique, face-on, etc.) may be taken from the same individual, allowing the system to match a patient in a variety of positions and/or angles. Each model body type in the database may also be normalized (e.g., scaled) so that they can be compared more reliably against each other and against patient pictures.

Figure 9:
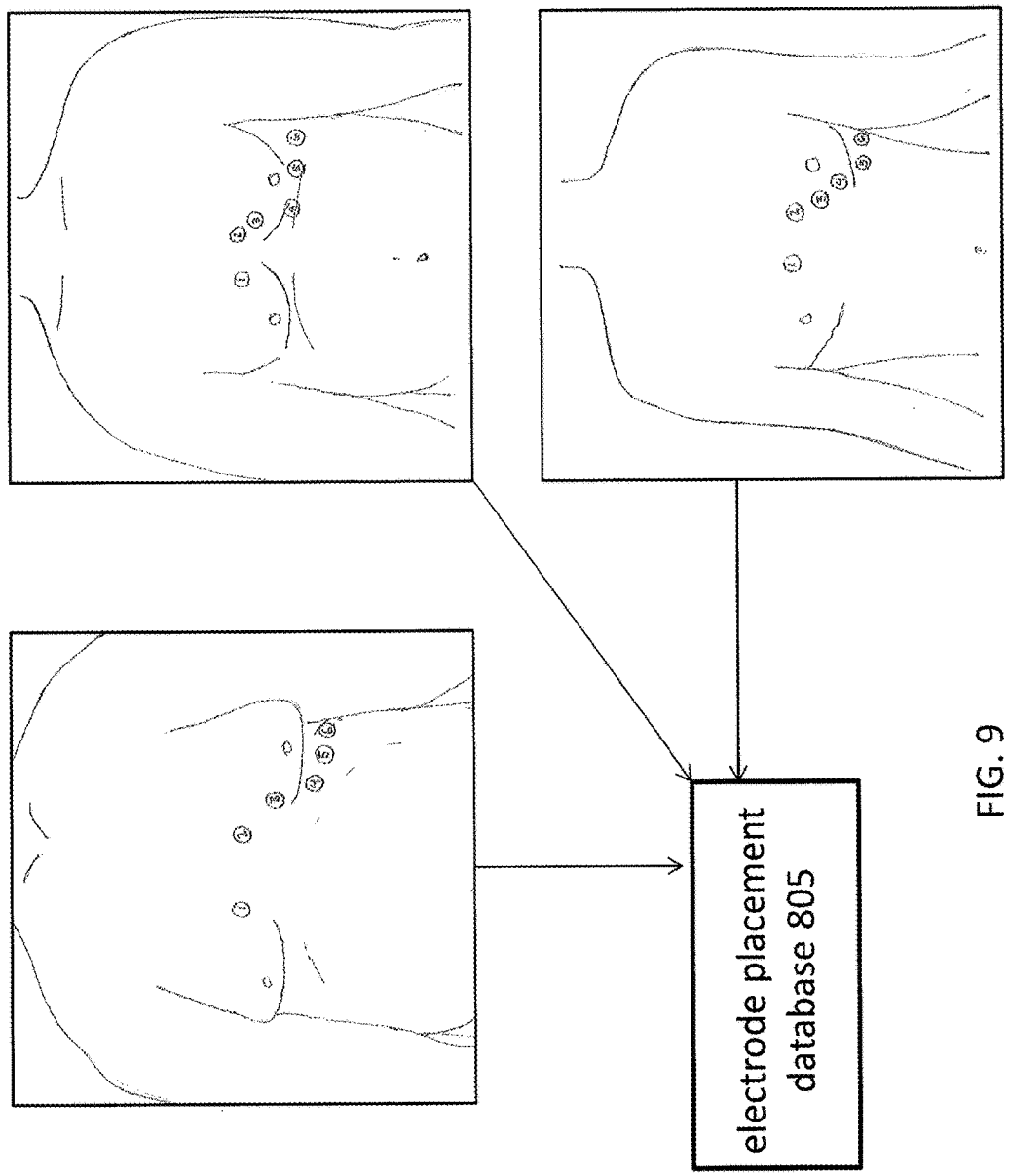
FIG. 9 illustrates exemplary representations of a plurality of body types and predetermined electrode placement positions corresponding to each body type forming part of one variation of an electrode placement database.

FIG. 9 shows an example of model body types with corresponding ECG electrodes, illustrating a variety of body morphologies that are part of the electrode placement database 805. For illustrative simplicity, only three examples are shown, though more may be included, as mentioned above. The database may also include male and female bodies, and a variety of different ages, ethnicities, sizes, etc.

In FIG. 9 the electrode placement database includes image of different body types with predetermined, conventional or standard electrode positions included in the image. In some variations the database may also or alternatively include body type characteristic information extracted from different body types, including different morphologies. For example, the database may include anatomical landmark characteristics (measurements). This information may be extracted from images such as those shown in FIG. 9. When comparing the patient picture to the database, the patient picture may have the same anatomical landmarks extracted for direct comparison with the database.

For example, in some embodiments, comparing the picture of the patient to the database can include comparing anatomical landmarks on the picture of the patient to anatomical landmarks in the database. As mentioned, anatomical landmarks can include the torso size, length, and configuration of a body region (e.g., torso). Anatomical landmarks may include the shoulder width and configuration, for example the size and shape of the clavicle. The anatomical landmarks can include the size and configuration of the arms and legs. The anatomical landmarks can include the chest size and width including the sternum, sternal notch, and rib configuration. The anatomical landmarks can include the size and configuration of the chest and ribs including the first, second, third, fourth, and fifth intercostal spaces, and the manubriosternal junction also referred to as the Angle of Louis, as much as they are detectable from the external anatomy apparent in the picture of the patient. The anatomical landmarks can include areas on the arms, legs, chest, neck, etc. Anatomical landmarks may also include the distances between various body regions. In some embodiments the fourth intercostal space can be determining from the manubriosternal junction. The fifth intercostal space, mid-clavicular line, left anterior axillary line, and left mid-axillary line can also be determined from the picture of the patient. In some embodiments the electrode placement can be determined based on the location of the fourth intercostal space, fifth intercostal space, mid-clavicular line, left anterior axillary line, and left mid-axillary line.

Figure 11:
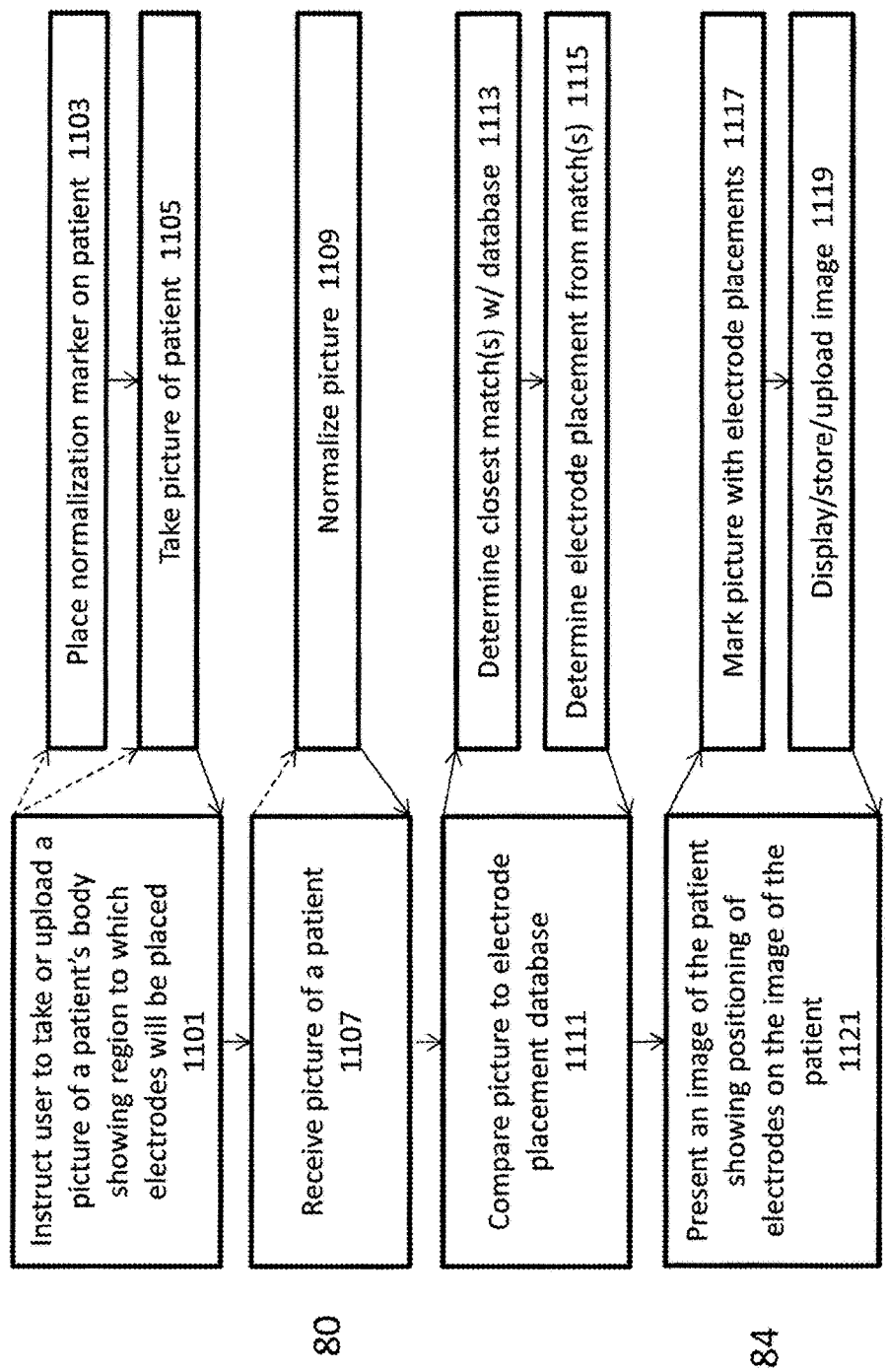
FIG. 11 is an exemplary flowchart describing a method for providing a user with guidance for placing electrodes in accordance with one embodiment.

FIG. 11 illustrates a method of guiding placement of electrodes on a patient. A system or device for guiding placement of electrode may be configured to perform all or some of these steps. For example, in some variations the user may be instructed to take or upload a picture of the patient 1101, and particularly the region of the body where the electrodes will be positioned. The device or system may include written instructions, spoken instructions and/or visual instructions to guide the user through the steps of taking or selecting a picture of the subject. For example, a handheld computer device (e.g., smartphone) may instruct the user to place a normalization (e.g., sizing) marker on the patient 1103, position the patient (e.g., lying down) and take a front-on picture of the patient's torso, including the marker 1105. In some variations the system or device may then ask the user to select the picture from the library of pictures, so that the picture is received by the system/device 1107.

The system or device may then pre-process the picture of the patient. Preprocessing may include normalizing the picture 1109. For example, if a normalizing marker is use, the picture may be scaled using the normalizing marker. Since the size of the normalizing marker is known, the system/device may analyze the picture to identify the normalizing marker, measure the length, and adjust the size of the picture using this measured length. The picture may also be cropped to remove any non-essential regions, and the picture may be adjusted to aid in comparing the picture to the electrode placement database. For example, the picture may be contrast enhanced. In some variations pre-processing may include extracting features (including anatomical landmarks, as discussed above.

The picture (or characteristic features extracted from the picture) may then be compared to the electrode placement database 1111 to determine one or more close matches with the body types in the database 1113. For example, the picture may be matched against the body types in the database to find the most similar body type or types. The predetermined, conventional/standard electrode placement from the one or more closest matches may then be used to determine electrode placement for the patient 1115. If there is a single close match, the electrode positioning for the closest match may be applied to the patient. For example, in variations in which the database includes images of the body types with predetermined conventional/standard electrode placement, the matching body type image may be aligned with and overlaid onto the patient image; in some variations all of the body type image except for the electrode positions may be removed, so that the placement of the electrode is shown in an image including the picture of the patient (in some variations, the normalized version of the picture). This picture may then be output (e.g., on a display screen on the handheld computing device).

In some variations multiple close matches from the database may be identified and used to determine conventional/standard electrode positions for the patient. For example, a weighted combination of the electrode positions (e.g., weighted by the similarity to the patient picture) may be used to determine the electrode positions on the patient picture.

In some variations comparing the patient picture to the database may be performed by a neural network that is trained in matching patient pictures to the database images. Thus, the network may determine which images are most closely matching. Similarly or alternatively, pattern recognition may be applied to match the picture of the patient (or extracted information from the picture) to the database (including extracted information) of body types.

As mentioned above, in some variations the system displays an image of the patient (e.g., taken from the picture of the patient) showing the conventional/standard positioning of the one or more electrodes on the patient 1121. Alternatively or in addition, the system may store or upload the image 1119 after preparing it 1117.

In some embodiments comparing the picture of the body to the database can be done on a remote server. In some embodiments comparing can be done on the computer device.

A system performing all or some of these steps typically includes control logic for controlling a processor and other system components to perform all or some of these steps. For example, in some embodiments the methods disclosed herein are performed by a computer program or software/hardware/firmware (or combinations thereof). The system may include software configured as an application for a smartphone or tablet computer that may control the operation of the system. Thus, all or some of the steps disclosed herein can be performed by the application on the smartphone or tablet computer. The smartphone application can include a user interface. For example, the smartphone application can receive a picture of the patient and present an image of the patient showing positioning of the electrodes.

A system or device for guiding electrode placement may therefore include control logic controlling the receipt of the patient picture (and in some variations, guiding the user in taking the picture), and for presenting the image including the patient showing marked locations for electrodes. The control logic may direct the picture of the patient to pre-processing and/or database comparison modules either on-board the system/device (e.g., using the smart phone processor) or remotely (e.g., sending the picture to a remote processor).

Figure 13:
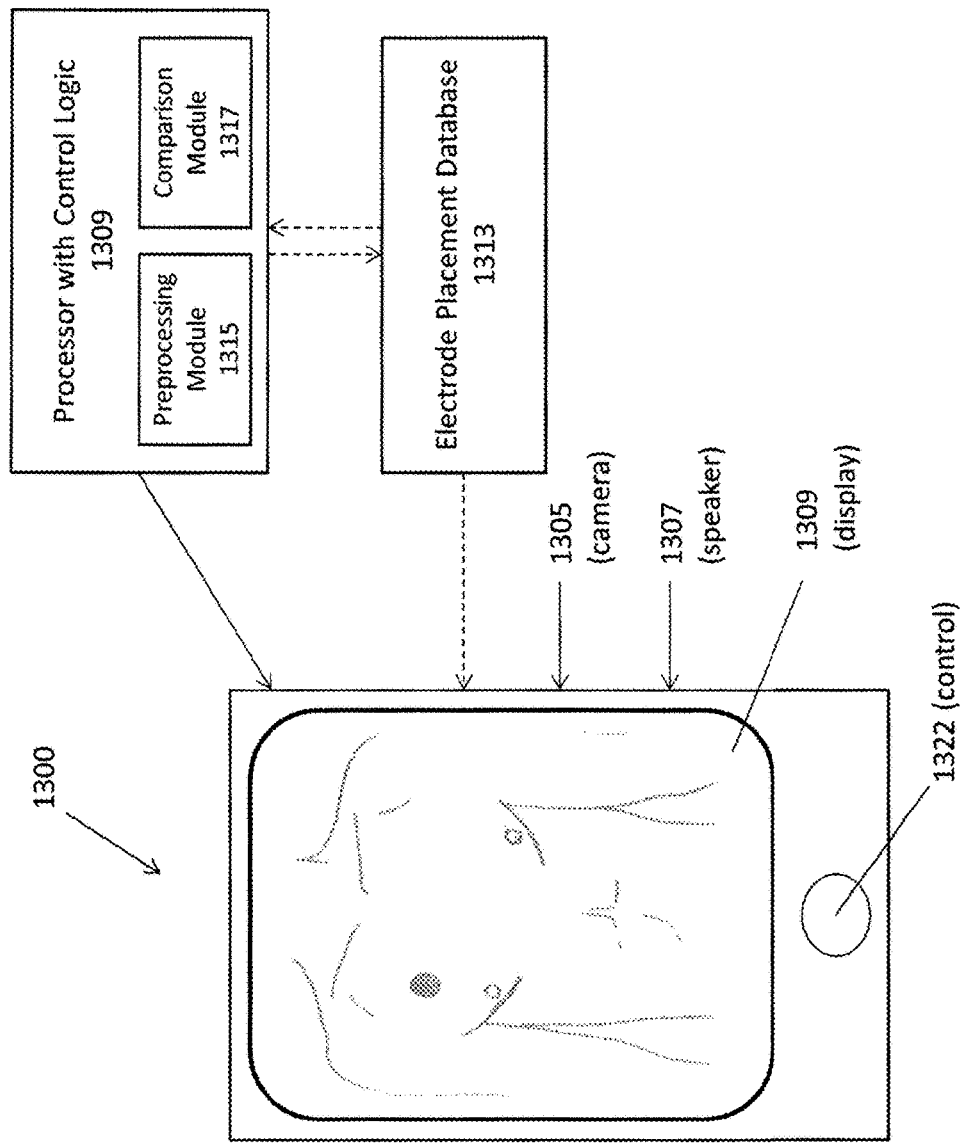
FIG. 13 illustrates one example of a system for guiding electrode placement.

FIG. 13 illustrates one example of a system for guiding electrode placement. In this example, the system includes control logic 1309 that is configured to run on a processor of a handheld computing device such as a smartphone 1300. The control logic may be downloadable (e.g., an application software). The control logic may guide the user through the process as mentioned above, including taking and/or selecting the picture of the user. The control logic may include a preprocessing module 1315 for normalizing and/or extracting features from the picture of the patient. The control logic may also include a comparison module 1317 for comparing the picture to an electrode placement database 1313. The database and these modules may be included as part of the control logic, or they may be separate from the control logic, but the control logic may control their operation, and may regulate the flow of information between them. In some variations one or more of the database 1313, preprocessing module 1315 and comparison module 1317 are external to the smartphone 1300, and may be part of an external database (not shown). The control logic may control the interaction with this external database (using, e.g., the smartphone network connectivity). The control logic may also regulate the operation of a camera 1305 that may be used to take the patient picture, and/or a speaker, display, and any other output for communicating with the user, and for displaying the generated image of the patient with the electrodes positions indicated. As mentioned, a mobile computing device may typically include a processor, display, and memory; the control logic may access these components in order to perform the functions described above.

Any of these systems may also include a normalization marker that may be used as indicated above.

In some embodiments a handheld computer device is used with the systems and methods disclosed herein. The handheld computer device can include a mobile telecommunications device, tablet computer (e.g. iPad™), or laptop computer. The mobile telecommunications device, tablet computer, or laptop computer can include a camera or be adapted to send/receive data with a camera. The mobile telecommunications device can include a cell phone or smartphone with a camera, such as an iPhone™, Android™, or other smartphone. In some embodiments a hand held camera can be used. The hand held camera can have network connectivity such that it can send and receive data over a wireless network (WiFi) or cellular network (3G, 4G, etc.).

In some embodiments the methods disclosed herein can be performed in whole or in part by firmware. In some embodiments the methods disclosed herein can be performed by a combination of firmware and software.

Images showing electrode placement can be presented to the patient or user. The images can be presented on a computer device. For example, the images can be presented on a smartphone, cell phone, laptop computer, tablet computer, digital camera, or home computer.

As mentioned above, in some embodiments comparing the picture of the patient with electrodes includes verifying the placement of the electrodes on the patient or providing further instructions to the patient to correct the electrode placement. The further instructions can include an image of the picture of the user showing the correct electrode placement or annotations to show the correction of the electrode placement. The further instructions can also include text or other instructions to correct the electrode placement, such as instructions to move a specific electrode by a determined amount or to a specific location.

In some embodiments the electrode configurations can correspond to the standard or conventional 10 electrode placement used for a 12-lead ECG with the arm and leg electrodes placed near the wrist and ankle. In some cases the electrodes on the presented image can be color coded to correspond with the colors used in the conventional 12-lead configuration.

In some embodiments the electrode configurations can correspond to 3-lead or 5-lead configurations. In some embodiments the electrode configurations can correspond to the Mason-Likar configuration or other non-conventional electrode configuration. In some embodiments the electrode configurations can be used to show the placement of $V_1$-$V_6$ only.

Conventional electrode placement for the 12-lead ECG places the electrodes on the left side of the body. In some cases it may be desirable to place the electrodes on the right side of the body. In some embodiments the electrode configuration can be on the right side of the body.

In some embodiments a second picture can be taken after the electrodes are placed on the patient using the image of the patient showing the electrode placement. A picture of the body of the patient with the electrodes placed on the patient can be taken. The picture of the body can be compared to the database to verify the placement of the electrodes. If the electrodes are in the predetermined location then the electrode placement is confirmed. If one or more electrodes are not in the predetermined positions then instructions to correct the electrodes can be determined. The instructions can include a modified image of the picture of the patient's body showing the correct electrode placement or an annotated picture of the body showing the electrodes that need to be moved.

After the electrodes are placed on the body of the patient the electrodes can be used to take an ECG. In some embodiments the ECG can be taken in a medical office, hospital, or ambulance. In some embodiments the ECG can be taken outside of a medical office, such as at the home of the patient.

In some embodiments, the electrodes can be attached to the computer device to take the ECG after the electrodes are placed on the patient. In some embodiments the electrodes can be attached to a device that can communicate with a smartphone or tablet computer. The smartphone or tablet computer can then be used to record electrical signals from the electrodes to take an ECG. The computer device can provide instructions for taking the ECG. The electrical signals can be analyzed to scan for errors such as switched electrodes or other problems discernible from the electrical signals. The ECG data can be recorded over a period of time and averaged to prepare an ECG for a representative heartbeat.

Additional examples of methods, systems and devices for guiding placement of electrodes according to a predetermined, conventional and/or standard electrode placement regime are briefly discussed below, in addition to the examples already provided above.

Example 1

Figure 12:
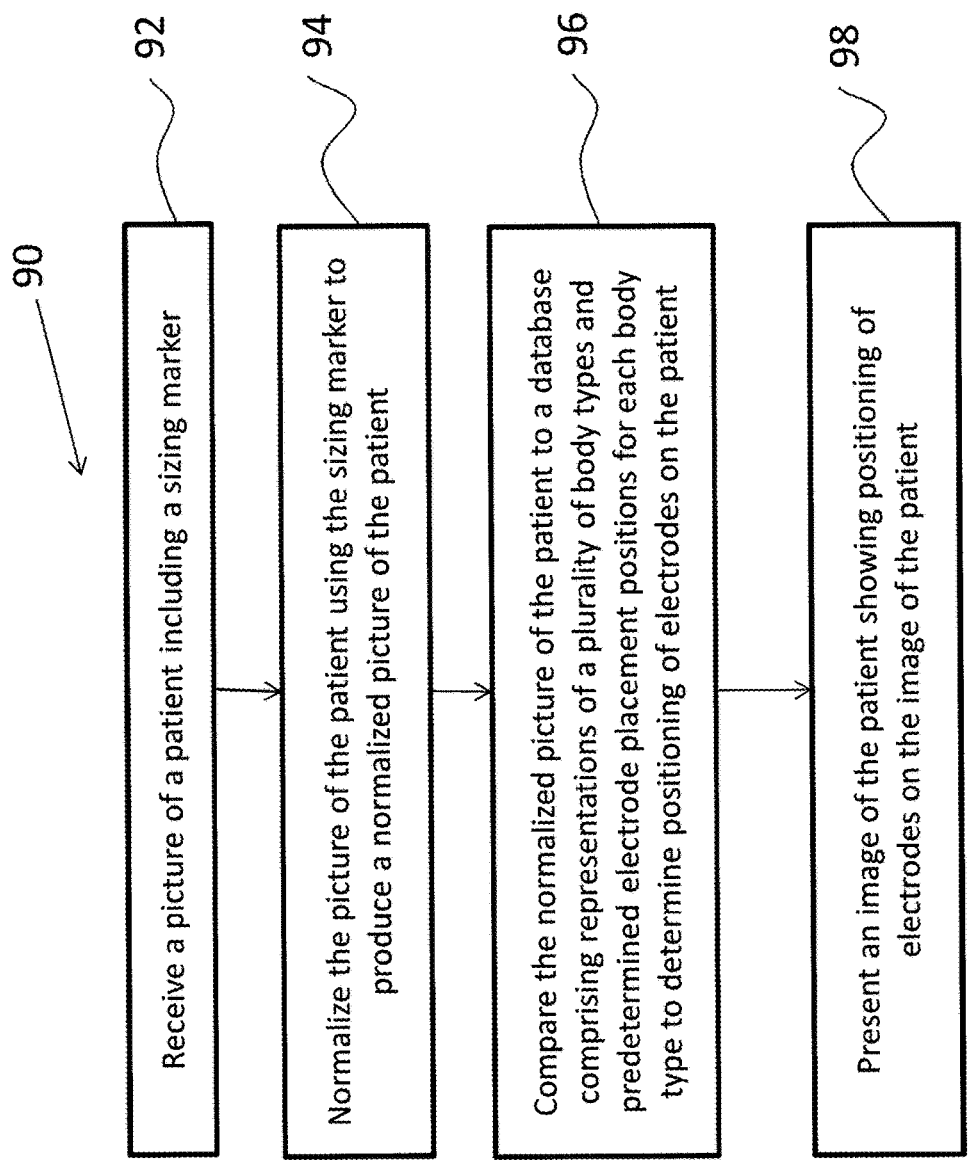
FIG. 12 is an exemplary flowchart of a method for determining the placement of electrodes on a patient in accordance with one embodiment.

FIG. 12 is a flowchart of one exemplary method 90 for determining the placement of electrodes on a patient. A picture of a patient including a sizing marker is received 92. The picture of the patient is normalized using the sizing marker to produce a normalized picture of the patient 94. The normalized picture of the patient is compared to a database comprising representations of a plurality of body types and predetermined electrode placement positions for each body type to determine positioning of electrodes on the patient 96. An image of the patient is then presented showing positioning of electrodes on the image of the patient 98.

The image can be presented on a handheld computer device such as a smartphone or tablet computer. The user or patient can place the electrodes based on the presented image. The electrodes can then be used to take an ECG.

Example 2

A smartphone can be used by an emergency medical technician (EMT) to take a picture of the chest of a patient. The picture of the patient can be selected by the EMT for use with the smartphone application. The smartphone application can then present an image of the patient showing the electrode placement on the image of the patient to the EMT. The EMT can then place electrodes on the body of the patient using the image of the patient showing the electrode placement. After placement of the electrodes the patient is ready to have an ECG taken. The ECG can be taken by the EMT or taken later.

Example 3

A smartphone or tablet computer can be used by a doctor or nurse in a medical office to take a picture of the patient. The picture of the patient can be selected by the doctor or nurse for use with the smartphone or tablet computer application. The smartphone or tablet computer application can then present an image of the patient showing the electrode placement on the image of the patient to the doctor or nurse. The doctor or nurse can place electrodes on the body of the patient using the image of the patient showing the electrode placement. After placement of the electrodes the patient is ready to have an ECG taken.

Example 4

A user can take a picture of their body using a smartphone while at home. The user can select their picture for use with a smartphone application. The smartphone or tablet computer application can then present an image of the user showing the electrode placement on the image. The user can place electrodes on their body using the image showing the electrode placement. After placement of the electrodes the user is ready to have an ECG taken.

Example 5

A user or patient can use the front-facing camera and display of the smartphone for guidance with placing electrodes in real time. The smartphone display can show the picture of the patient's body taken by the front-facing camera in real time along with the predetermined electrode placement overlaid on the real time picture of the patient's body.

Example 6

A database containing information on electrode placement for various body types can be prepared. Methods for preparing the database can include taking a picture of the body of a test subject having electrodes placed on the body, analyzing the pictures of the bodies of the test subjects, categorizing the electrode placement data based on the anatomical landmarks on the test subjects, and generating a database containing electrode placement data based on body type and anatomical landmarks.

The database can be prepared by analyzing pictures of patients having electrodes correctly placed on their body. The electrode placement can be analyzed and quantified in relation to anatomical landmarks on the bodies of the patients.

The data for each patient can be classified based on any of the data collected. For example, the data can be classified based on body type, weight, height, gender, size, age, body mass index, etc. The data collected for the database can include the distance and direction between the areas for the desired electrode placement and anatomical landmarks.

The methods for generating the database can include taking pictures of each patient with and without the electrodes placed on the body.

From the above descriptions, it is clear that the presently disclosed and claimed inventive concept(s) are well-adapted to carry out the objects and to attain the advantages mentioned herein. While the presented embodiments have been described for purposes of this disclosure, it will be understood that numerous changes may be made which will readily suggest themselves to those skilled in the art and which are accomplished within the spirit of the presently disclosed and claimed inventive concepts.

What may be claimed is:

1. A system for guiding proper placement of electrocardiogram (ECG) electrodes on a patient, the system comprising:
   a camera configured to take a picture of the patient;
   a normalization marker configured to be placed on the patient;
   an electrode placement database wherein the electrode placement database comprises representations of a plurality of body types and predetermined electrode placement positions corresponding to each body type;
   a processor; and a non-transitory computer readable storage medium encoded with a computer program including instructions executable by the processor to cause the processor to:
    take a picture of the patient and the normalization marker when the normalization marker is positioned on the patient using the camera;
    normalize the picture of the patient using the normalization marker positioned on the patient in the picture;
    carry out a comparison of the normalized picture of the patient to the electrode placement database;
    determine positions of the electrodes on the patient from the comparison;
    generate an image of the patient showing the determined positions of the electrodes on the image of the patient; and
    present the image to the patient.

2. The system of claim 1, wherein to carry out the comparison of the normalized picture to the electrode placement database comprises determining the standard placement of the electrodes for a 12-lead ECG on the patient.

3. The system of claim 1, wherein to normalize the picture comprises scaling the picture.

4. The system of claim 1, wherein to carry out the comparison of the normalized picture of the patient to the electrode placement database includes determining the closest match between the picture and a representative body type in the patient database.

5. The system of claim 1, wherein to carry out the comparison of the normalized picture of the patient to the electrode placement database comprises interpolating between the closest matches to the picture and two or more representative body types in the patient database.

6. The system of claim 1, wherein to carry out the comparison of the normalized picture of the patient to the electrode placement database includes determining anatomical landmarks from the picture and comparing the anatomical landmarks to the electrode placement database.

7. The system of claim 1, wherein to carry out the comparison of the normalized picture of the patient to the database comprises using pattern recognition to determine the closest match between the picture and a representative body type in the database.

8. The system of claim 1, comprising a handheld computer device, and wherein to present the image of the patient showing positions for the electrodes on the image of the patient comprises presenting the image on the handheld computer device.

9. The system of claim 8, wherein the handheld computer device is a mobile phone, smartphone, or tablet computer with network connectivity.

10. The system of claim 1, wherein the computer program includes instructions executable by the processor that cause the processor to take the picture of the patient using the camera.

11. The system of claim 1, wherein to carry out the comparison of the normalized picture of the patient to an electrode placement database comprises comparing the picture of the patient having one or more electrodes already placed on the patient's chest to the electrode placement database.

12. The system of claim 11, wherein the computer program includes instructions executable by the processor that cause the processor to verify the position of the one or more electrodes already placed on the patient's chest.

13. The system of claim 12, wherein to present the image comprises presenting a corrected positioning of electrodes on the image of the patient.

14. The system of claim 1, wherein the computer program includes instructions executable by the processor that cause the processor to take the picture of the patient and the normalization marker.

\* \* \* \* \*